United States Patent
Osborne et al.

(10) Patent No.: US 6,537,806 B1
(45) Date of Patent: Mar. 25, 2003

(54) COMPOSITIONS AND METHODS FOR TREATING DIABETES

(75) Inventors: William R. A. Osborne, Seattle, WA (US); Nagarajan Ramesh, Santa Clara, CA (US)

(73) Assignee: University of Washington, Seattle, WA (US)

( * ) Notice: Subject to any disclaimer, the term of this patent is extended or adjusted under 35 U.S.C. 154(b) by 0 days.

(21) Appl. No.: 09/185,852

(22) Filed: Nov. 4, 1998

Related U.S. Application Data

(60) Provisional application No. 60/087,660, filed on Jun. 2, 1998.

(51) Int. Cl.[7] .......................... C12N 5/00; C12N 15/00; C12P 21/06; A01N 25/00; A61K 38/28
(52) U.S. Cl. .......................... 435/325; 514/866; 514/3; 435/320.1; 435/69.1
(58) Field of Search .............................. 435/69.1, 320.1, 435/325; 514/866, 3

(56) References Cited

U.S. PATENT DOCUMENTS

| | | | |
|---|---|---|---|
| 5,993,799 A | 11/1999 | Newgard | 424/93.21 |
| 6,048,524 A | 4/2000 | Selden et al. | 424/93.21 |

FOREIGN PATENT DOCUMENTS

| | | |
|---|---|---|
| WO | WO 92/21756 | 12/1992 |
| WO | WO 95/25547 | 9/1995 |
| WO | WO 96/31242 | 10/1996 |
| WO | WO 96/32489 | 10/1996 |
| WO | WO 96/40175 | 12/1996 |
| WO | WO 97/46590 | 12/1997 |

OTHER PUBLICATIONS

Gros et al., "Regulated production of mature insulin by non–βcells," *Human Gene Therapy* 8:2249–2259 (1997).

Vollenweider et al., "Processing of proinsulin by Furin, PC2, and PC3 in (Co) transfected COS (Monkey Kidney) cells," *Diabetes* 44:1075–1080 (1995).

Ali et al., Preventing Gastroepiploic Artery Spasm: Papaverine vs Calcium Channel Blockade, *J. Surgical Research*, 74:41–45 (1997).

Becker et al., Use of Recombinant Adenovirus for Metabolic Engineering of Mammalian Cells, *Methods in Cell Biol.*, 43:161–189 (1994).

Dale et al., A Randomized Controlled Phase III Trial of Recombinant Human Granulocyte Colony–Stimulating Factor (Filgrastim) for Treatment of Severe Chronic Neutropenia, *Blood*, 81(10) :2496–2502 (1993).

Dale et al., Cyclic Neutropenia: A Clinical Review, *Blood Reviews*, 2:178–185 (1988).

Daniels et al., Glucose Regulation of Transforming Gowth Factor–α Expression is Mediated by Products of the Hexosamine Biosynthesis Pathway, *Mol. Endocrinol.*, 7(8) : 1041–1048 (1993).

Shimon Efrat, Genetic engineering of β–cells for cell therapy of diabetes: cell growth, function, and immunogenicity, *Diabetes Reviews*, 4(2):224–234 (1996).

Geary et al., Gene Transfer in Baboons Using Prosthetic Vascular Grafts Seeded with Retrovirally Transduced Smooth Muscle Cells: A Model for Local and Systemic Gene Therapy, *Hum. Gene Ther.*, 5: 1211–1216 (1994).

Gros et al., Regulated Production of Mature Insulin by Non–β–Cells, *Human Gene Therapy*, 8: 2249–2259 (1997).

Groskreutz et al., Genetically Engineered Proinsulin Constitutively Processed and Secreted as Mature, Active Insulin, *J. Biol. Chem.*, 269(8):6241–6245 (1994).

Hock et al., Expression of Human Adenosine Deaminase From Various Strong Promoters After Gene Transfer Into Human Hematopoietic Cell Lines, *Blood*, 74(2):876–881 (1989).

Hosaka et al., Arg–X–Lys/Arg–Arg Motif as a Signal for Precursor Cleavage Catalyzed by Furin within the Constitutive Secretory Pathway, *J. Biol. Chem.*, 266(19):12127–12130 (1991).

Kawakami et al., Subcutaneous Xenotransplantation of Hybrid Artificial Pancreas Encapsulating Pancreatic B Cell Line (MIN6): Functional and Histological Study, *Cell Transplant*, 6(5):541–545 (1997).

Kolodka et al., Gene therapy for diabetes mellitus in rats by hepatic expression of insulin, *Proc. Natl. Acad. Sci. USA*, 92 : 3293–3297 (1995).

Lejnieks et al., Granulocyte Colony Stimulating Factor Expression from Transduced Vascular Smooth Muscle Cells Provides Sustained Neutrophil Increases in Rats, *Hum. Gene Ther.*, 7:1431–1436 (1996).

McClain et al., Hexosamines and Insulin Resistance, *Diabetes*, 45:1003–1009 (1996).

(List continued on next page.)

Primary Examiner—Anthony C. Caputa
Assistant Examiner—Gary B. Nickol
(74) Attorney, Agent, or Firm—Campbell & Flores LLP

(57) ABSTRACT

The present invention provides an isolated population of cells containing an expressible nucleic acid encoding proinsulin containing a proinsulin cleavage site and a glucose-regulated expressible nucleic acid encoding a protease capable of cleaving the proinsulin cleavage site to produce insulin. The invention also provides an isolated population of cells which further express a hexosamine synthetic pathway enzyme. The invention additionally provides vectors containing an expressible nucleic acid encoding proinsulin containing a proinsulin cleavage site and a glucose-regulated expressible nucleic acid encoding a protease capable of cleaving the proinsulin cleavage site to produce insulin. The invention further provides a method of treating or preventing diabetes by implanting into an individual cells coexpressing proinsulin containing a proinsulin cleavage site and a glucose-regulated protease capable of cleaving the proinsulin cleavage site to produce insulin.

15 Claims, 3 Drawing Sheets

OTHER PUBLICATIONS

McClain et al., Glucose and glucosamine regulate growth factor gene expression in vascular smooth muscle cells, *Proc. Natl. Acad. Sci. USA*, 89: 8150–8154 (1992).

McKnight et al., Molecular Cloning, cDNA Sequence, and Bacterial Expression of Human Glutamine:Fructose–6–phosphate Amidotransferase, *J.Biol.Chem.*, 267(35) :25208–25212 (1992).

Christopher B. Newgard, Cellular Engineering and Gene Therapy Strategies for Insulin Replacement in Diabetes, *Diabetes*, 43:341–350 (1994).

Odagiri et al., Function of the Human Insulin Promoter in Primary Cultured Islet Cells, *J. Biol. Chem.*, 271(4):1909–1915 (1996).

Osborne et al., Design of vectors for efficient expression of human purine nucleoside phosphorylase in skin fibroblasts from enzyme–deficient humans, *Proc. Natl. Acad. Sci. USA*, 85 :6851–6855 (1988).

Osborne et al., Transduced vascular smooth muscle cells in a canine model of gene therapy, *Clinical Res.* 41(2):194A (1993).

Osborne et al., Gene therapy for long–term expression of erythropoietin in rats, *Proc. Natl. Acad. Sci. USA*, 92:8055–8058 (1995).

Osborne et al., Long Term Expression of Human of Human Adenosine Deaminase in Mice After Transplantation of Bone Marrow Infected with Amphotropic Retroviral Vectors, *Hum. Gene Ther.*, 1:31–41 (1990).

Raja et al., Transcriptional Regulation of the Human Transforming Growth Factor–α Gene, *Mol. Endocrinol.*, 5(4):514–520 (1991).

Ramesh et al., High–titer bicistronic retroviral vectors employing foot–and–mouth disease virus internal ribosome entry site, *Nucleic Acids Res.*, 24(14):2697–2700, (1996).

Sayeski et al., The murine glutamine:fructose–6–phosphate amidotransferas–encoding cDNA sequence, *Gene*, 140:289–290 (1994).

Scharp et al., Protection of Encapsulated Human Islets Implanted without Immunosuppression in Patients With Type I or Type II Diabetes and in Nondiabetic Control Subjects, *Diabetes*, 43:1167–1170 (1994).

Schuppin et al., Specific co–ordinated regulation of PC3 and PC2 gene expression with that of preproinsulin in insulin–producing βTC3 cells, *Biochem. J.*, 313:259–268 (1996).

Smeekens et al., Proinsulin processing by the subtilisin–related proprotein convertases furin, PC2, and PC3, *Proc. Natl. Acad. Sci. USA*, 89:8822–8826 (1992).

Stockschlaeder et al., L–Histidinol Provides Effective Selection of Retrovirus–Vector–Transduced Keratinocytes Without Impairing Their Proliferative Potential, *Hum. Gene Ther.*, 2:33–39 (1991).

Sugiyama et al., Defective Adenoassociated Viral–Mediated Transfection of Insulin Gene by Direct Injection Into Liver Parenchyma Decreases Blood Glucose of Diabetic Mice, *Horm. Metab. Res.*, 29:599–603 (1997).

Wang et al., An encapsulation system for the immunoisolation of pancreatic islets, *Nature Biotech.*, 15:358–362 (1997).

Yanagita et al., Processing of mutated proinsulin with tetrabasic cleavage sites to bioactive insulin in the non–endocrine cell line, COS–7, *FEBS Letters*, 311(1):55–59 (1992).

Zhou et al., In vitro and in vivo evaluation of insulin–producing βTC6–F7 cells in microcapsules, *Am. J. Physiol.*, 274 (*Cell Physiol.* 43):C1356–C1362 (1998).

Naffakh et al, "Sustained delivery of erythropoietin in mice by genetically modified skin fibroblasts," *Proc. Natl. Acad. Sci USA*, 92:3194–3198 (1995).

XP002131707 & JP08033472A (Terumo Corp.), Feb. 6, 1996 (Apr. 6, 1996) abstract.

Smeekens et al. (PNAS, vol. 89, pp. 8822–8826, 1992).*

Lu et al. (FEBS Letters, vol. 399: pp. 37–42, 1996).*

Morgan et al. (Nucleic Acids Research, 1992, V.20(6), pp. 1293–1299).*

Walther et al., J. Mol. Med., vol. 74, pp. 379–392, 1996.*

Morgan et al. , 1992, Nucleic Acids Research, V.20(6),pp. 1293–1299.*

* cited by examiner

```
gctgcatcag aagaggccat caagcacatc actgtccttc tgcc atg gcc ctg tgg    56
                                              Met Ala Leu Trp
                                               1 atg cgc ctc ctg ccc ctg ctg gcg ctg ctg gcc ctc tgg gga cct gac   104
Met Arg Leu Leu Pro Leu Leu Ala Leu Leu Ala Leu Trp Gly Pro Asp
 5              10              15              20 cca gcc gca gcc ttt gtg aac caa cac ctg tgc ggc tca cac ctg gtg   152
Pro Ala Ala Ala Phe Val Asn Gln His Leu Cys Gly Ser His Leu Val
                25              30              35 gaa gct ctc tac cta gtg tgc ggg gaa cga ggc ttc ttc tac aca ccc   200
Glu Ala Leu Tyr Leu Val Cys Gly Glu Arg Gly Phe Phe Tyr Thr Pro
            40              45              50 aag acc cgc cgg gag gca gag gac ctg cag gtg ggg cag gtg gag ctg   248
Lys Thr Arg Arg Glu Ala Glu Asp Leu Gln Val Gly Gln Val Glu Leu
        55              60              65 ggc ggg ggc cct ggt gca ggc agc ctg cag ccc ttg gcc ctg gag ggg   296
Gly Gly Gly Pro Gly Ala Gly Ser Leu Gln Pro Leu Ala Leu Glu Gly
    70              75              80 tcc ctg cag aag cgt ggc att gtg gaa caa tgc tgt acc agc atc tgc   344
Ser Leu Gln Lys Arg Gly Ile Val Glu Gln Cys Cys Thr Ser Ile Cys
 85              90              95             100 tcc ctc tac cag ctg gag aac tac tgc aac tag acgcagcccg caggcagccc  397
Ser Leu Tyr Gln Leu Glu Asn Tyr Cys Asn
                105             110 cccacccgcc gcctcctgca ccgagagaga tggaataaag cccttgaacc agc         450
```

Fig. 4

COMPOSITIONS AND METHODS FOR TREATING DIABETES

This application claims the benefit of U.S. Provisional Application No. 60/087,660, filed Jun. 2, 1998, and is incorporated herein by reference.

This invention was made with government support under grant number DK43727 and DK50686 awarded by the National Institutes of Health. The United States Government has certain rights in this invention.

BACKGROUND OF THE INVENTION

The present invention relates generally to methods for the treatment and prevention of diabetes and to the use of cells which can express insulin in a glucose-regulated manner for this treatment.

In an individual with normal regulation of blood glucose, the pancreatic hormone insulin is secreted in response to increased blood sugar levels. Increased blood glucose generally occurs following a meal and results from insulin action on peripheral tissues such as skeletal muscle and fat. Insulin stimulates cells of these peripheral tissues to actively take up glucose from the blood and convert it to forms for storage. This process is also referred to as glucose disposal. The levels of blood glucose vary from low to normal to high throughout the day within an individual, depending upon whether the person is in the fasting, intermediate, or fed state. These levels are also referred to as hypoglycemia, euglycemia and hyperglycemia, respectively. In the diabetic individual, these changes in glucose homeostasis are disregulated due to either faulty insulin secretion or action, resulting in a chronic state of hyperglycemia.

Diabetes mellitus is a common disorder, with a prevalence of about 4–5%. The risk of developing diabetes increases with increased weight, with as many as 90% of adult onset diabetic patients being obese. Therefore, due to the high incidence of obese adults, the incidence of adult onset diabetes is increasing worldwide. Diabetes mellitus is classified into three major forms. Type 2 diabetes is one form and is also referred to as non-insulin dependent diabetes (NIDDM) or adult-onset diabetes. Type 1 diabetes is the second form and is referred to as insulin-dependent diabetes (IDDM). The third type of diabetes is genetic and is due to mutations in genes controlling pancreatic islet beta (β) cell function. Although the diagnosis of diabetes is based on glucose measurements, accurate classification of all patients is not always possible. Type 2 diabetes is more common among adults and type 1 diabetes dominates among children and teenagers.

Diabetes mellitus of both types 1 and 2 are associated with a shortened life expectancy as well as other complications such as vascular disease and atherosclerosis. Long-term management of diabetes to prevent late complications often includes insulin therapy regardless of whether the patients are classified as type 1 or type 2. Type 1 diabetes is an auto-immune disease which is associated with near complete loss of the insulin producing pancreatic β cells. This loss of β cells results in insulin-dependence for life. Type 1 diabetes can occur at any age and it has been estimated that about 1% of all newborns will develop this disease during their lifetime.

Insulin is first synthesized as a precursor and cleaved through the action of proteases to form a mature, bioactive molecule that consists of two subunits covalently bonded together. Insulin function and regulation have been studied in regard to both therapeutic and research applications. For example, insulin has been produced for therapeutic purposes by recombinant expression using modified cells. As a research tool, insulin was the first protein to be chemically synthesized and also has been used to study secretory pathways and the regulation of secretory mechanisms.

A widely used method of treatment for type 1 diabetes and to some extent type 2 diabetes has classically consisted of insulin maintenance therapy. Such therapy in its simplest form requires the injection of purified or recombinant insulin into a patient following ingestion of a meal or at regular intervals throughout the day to maintain normal blood glucose levels. These injections are required ideally at a frequency of four times per day. Although the above method of treatment provides some benefit to the patient, this method of insulin therapy nevertheless suffers from inadequate blood glucose control as well as requiring a great deal of patient compliance.

Another method of treatment for type 1 diabetes includes the use of devices such as an insulin pump which allows for the scheduled delivery of insulin. This method can be preferable to the method described above due to the need for less frequent injections. However, the use of an insulin pump therapy also has drawbacks in that replacement of a needle once every three days is still required. Similar to insulin maintenance therapy, the insulin pump method also does not achieve optimal glucose regulation as the delivery of insulin is not regulated in response to changes in blood glucose level. These methods of treating diabetes are therefore burdensome as well as inadequate. Furthermore, although these methods can provide some benefit for reducing symptoms of diabetes, none have been completely effective over the course of an average adult lifetime and none have been shown to be effective in preventing this disease.

Various approaches of cell therapy for replacing bioactive insulin into a diabetic individual have been attempted. These include gene therapy approaches, immunotherapies and use of artificial β-cells.

In vivo gene therapy for insulin expression has included liver targeted retroviral-mediated transduction in rats and adenoassociated virus administration to mice (Kolodka et al., *Proc. Natl. Acad. Sci. USA* 92:3293–3297 (1995); Sugiyama et al., *Horm. Metab. Res.* 29:599–603 (1997)). However, these approaches did not provide glucose-regulated insulin delivery and have limited applications in patients.

Treatment for diabetes has also included studies attempting to manipulate the immune system. In particular, to reverse the autoreactivity against the beta cell specific autoantigens, insulin or glutamic acid decarboxylase (GAD65) have been injected into young diabetes-prone NOD mice or BB rats (Kaufman et al., *J. Clin. Invest.* 89:283–292 (1992); Kaufman et al., *Nature* 366:69–72 (1993); Bieg et al., *Diabetologia* 40:786–792 (1997)). Reversal of autoreactivity against beta cell specific autoantigens has also been attempted with nasal administration of GAD65 peptides (Tian et al., *J. Exp. Med.* 183:1561–1567 (1996)).

Genetic modification of pancreatic islet β-cells and generation of artificial beta cells are approaches for the treatment of diabetes by cell therapy (Becker et al., *Methods Cell Biol.* 43:161–189 (1994); Efrat, *Diabetes Reviews* 4:224–234 (1996); Newgard, *Diabetes* 43:341–350 (1994); Gros et al., *Hum. Gene Ther.* 8:2249–2259 (1997); Taniguchi et al., *J. Surg. Res.* 70:41–45 (1997). Xenograft and even allogeneic cell delivery to express insulin require cell encapsulation to prevent host immune responses, and problems with cell survival and sustained insulin delivery have been identified (Kawakami et al., *Cell Transplant.* 6:541–545 (1997); Wang et al., *Nature Biotechnol.* 15:358–362 (1997); Zhou et al., *Am. J. Physiol.* 274:C1356–C1362 (1998); Scharp et al., *Diabetes* 43:1167–1170 (1994)).

Pancreatic and islet transplantation has also been attempted as a treatment for diabetes. Use of this treatment has shown limited success due to the requirement for matched tissue from 2–5 adult donors per recipient. This method has also lacked success due, in part, to the failure of the transplanted tissue to maintain normal glucose-regulated insulin secretion and to remain viable over a reasonable period of time.

Thus, there exists a need for simple and more efficient methods that can regulate glucose homeostasis in a diabetic individual in a way that more closely mimics a normal endogenous insulin response. The present invention satisfies this need and provides additional advantages.

SUMMARY OF THE INVENTION

The present invention provides an isolated population of cells containing an expressible nucleic acid encoding proinsulin containing a proinsulin cleavage site and a glucose-regulated expressible nucleic acid encoding a protease capable of cleaving the proinsulin cleavage site to produce insulin. The invention also provides an isolated population of cells which further express a hexosamine synthetic pathway enzyme. The invention additionally provides vectors containing an expressible nucleic acid encoding proinsulin containing a proinsulin cleavage site and a glucose-regulated expressible nucleic acid encoding a protease capable of cleaving the proinsulin cleavage site to produce insulin. The invention further provides a method of treating or preventing diabetes by implanting into an individual cells coexpressing proinsulin containing a proinsulin cleavage site and a glucose-regulated protease capable of cleaving the proinsulin cleavage site to produce insulin.

BRIEF DESCRIPTION OF THE DRAWINGS

FIG. 4 shows the nucleotide and amino acid sequences of human proinsulin cDNA (SEQ ID NOS:1 and 2, respectively; GenBank accession No. X70508; Chekhranova et al., *Mol. Biol.* 26:596–600 (1992)). The A-chain of human insulin corresponds to nucleotides 312–374 (SEQ ID NO:3) and amino acids 90–110 (SEQ ID NO:4). The B-chain of human insulin corresponds to nucleotides 117–206 (SEQ ID NO:5) and amino acids 25–54 (SEQ ID NO:6).

DETAILED DESCRIPTION OF THE INVENTION

Figure 1:
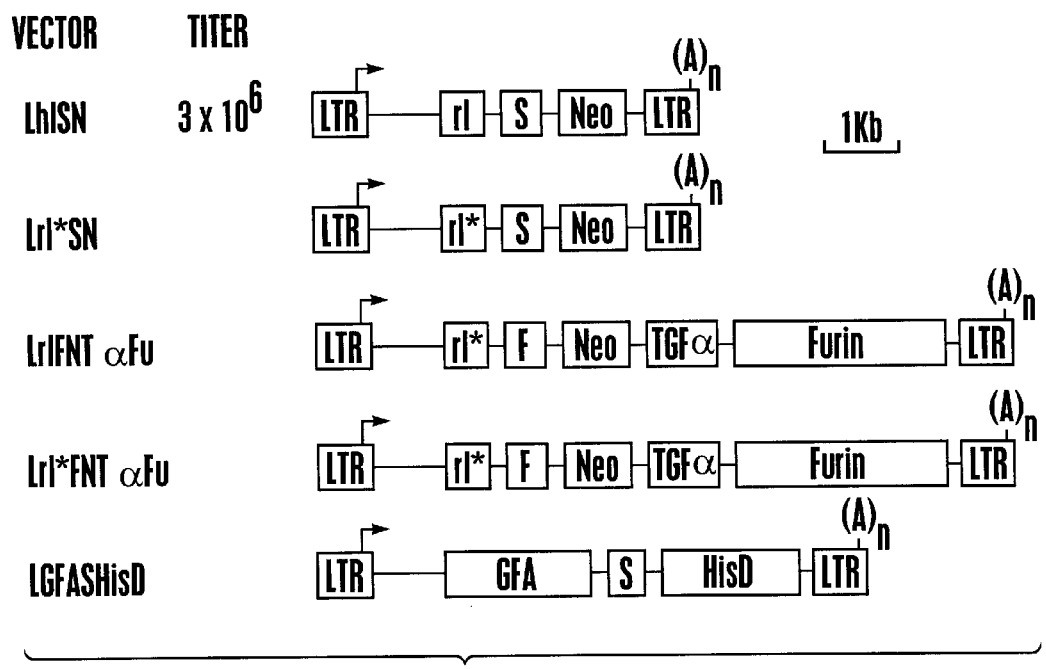
FIG. 1 shows vectors expressing proinsulin, proinsulin and glucose-regulated furin, and glutamine:fructose-6-phosphate amidotransferase.

This invention is directed to cell populations and methods for treating or preventing diabetes. The cell populations contain nucleic acids encoding proinsulin containing a proinsulin cleavage site and a protease capable of cleaving the proinsulin cleavage site. The methods of the invention are directed to implanting the above cell populations into diabetic individuals for the therapeutic production of insulin. An advantage of the cell populations and their use in treating diabetes is that the proinsulin and protease are coexpressed, with expression of the protease under glucose regulation. This regulated coexpression results in the amplification of secreted bioactive insulin in a glucose-responsive manner.

In one embodiment, implantable, non-endocrine cells such as vascular smooth muscle cells are constructed to express proinsulin and a protease. These cells exhibit the ability to secrete high levels of glucose-regulated mature insulin and are constructed by transduction of the cells with a three-gene retroviral vector. The three-gene retroviral vector contains elements required for the constitutive expression of proinsulin and the glucose-regulated expression of the protease, furin. Regulated expression of furin is under the control of a glucose-responsive transforming growth factor α (TGFα) promoter and regulatory element. The retroviral vector also encodes for the selectable marker neomycin phosphotransferase, which allows for the positive selection of cells transduced with and expressing the vector. Exposure of the population of transduced vascular smooth muscle cells to a high glucose environment results in secretion of bioactive insulin at levels that are sufficient for treating diabetes.

In a second embodiment of the invention, the above described smooth muscle cells expressing glucose-regulated insulin are further modified to express the hexosamine biosynthetic pathway enzyme glutamine:fructose-6-phosphate amidotransferase. Expression of this additional gene further enhances expression of the protease, which allows for enhanced processing of proinsulin to mature insulin. Implantation of these modified cells into the stomach wall of a diabetic animal is achieved using a prosthetic graft made of a biocompatible material such as polytetrafluoroethylene (PTFE). Glucose-regulated insulin expression from these smooth muscle cells engrafted into a diabetic individual allows for glucose homeostasis in that individual sufficient to provide therapeutic benefit.

As used herein, the term "diabetes" is intended to mean the diabetic condition known as diabetes mellitus. Diabetes mellitus is a chronic disease characterized by relative or absolute deficiency of insulin which results in glucose intolerance. The term is intended to include all types of diabetes mellitus, including, for example, type I, type II, and genetic diabetes. Type I diabetes is also referred to as insulin dependent diabetes mellitus (IDDM) and also includes, for example, juvenile-onset diabetes mellitus. Type I is primarily due to the destruction of pancreatic β-cells. Type II diabetes mellitus is also known as non-insulin dependent diabetes mellitus (NIDDM) and is characterized, in part, by impaired insulin release following a meal. Insulin resistance can also be a factor leading to the occurrence of type II diabetes mellitus. Genetic diabetes is due to mutations which interfere with the function and regulation of β-cells.

Diabetes is characterized as a fasting level of blood glucose greater than or equal to about 140 mg/dl or as a plasma glucose level greater than or equal to about 200 mg/dl as assessed at about 2 hours following the oral administration of a glucose load of about 75 g. The term "diabetes" is also intended to include those individuals with hyperglycemia, including chronic hyperglycemia and impaired glucose tolerance. Plasma glucose levels in hyperglycemic individuals include, for example, glucose concentrations greater than normal as determined by reliable diagnostic indicators. Such hyperglycemic individuals are at risk or predisposed to developing overt clinical symptoms of diabetes mellitus.

As used herein, the term "treating" is intended to mean an amelioration of a clinical symptom indicative of diabetes. Amelioration of a clinical symptom includes, for example, a decrease in blood glucose levels or an increase in the rate of glucose clearance from the blood in the treated individual compared to pretreatment levels or to an individual with diabetes. The term "treating" also includes an induction of a euglycemic response in the individual suffering from disregulated hyperglycemia. Euglycemia refers to the range of blood glucose levels clinically established as normal, or as above the range of hypoglycemia but below the range of hyperglycemia. Therefore, a euglycemic response refers to the stimulation of glucose uptake to reduce the plasma glucose concentration to normal levels. For most adults, this level corresponds to the range in concentration of about 60–105 mg/dL of blood glucose and preferably between about 70–100 mg/dL, but can vary between individuals depending on, for example, the sex, age, weight, diet and overall health of the individual. Effective treatment of a diabetic individual, for example, would be a reduction in that individual's hyperglycemia, or elevated blood glucose levels, to normalized or euglycemic levels, with this reduction directly resulting from secretion of insulin. Alternatively, effective treatment would be a reduction in fasting blood glucose to levels less than or equal to about 140 mg/dL.

The term "treating" is also intended to include the reduction in severity of a pathological condition or a chronic complication which is associated with diabetes. Such pathological conditions or chronic complications are listed in Table 1 and include, for example, muscle wasting, ketoacidosis, glycosuria, polyuria, polydipsia, diabetic microangiopathy or small vessel disease, atherosclerotic vascular disease or large vessel disease, neuropathy and cataracts.

TABLE 1

Pathological Conditions Associated with Diabetes

Kidney

| | |
|---|---|
| Glomerular microangiopathy | Renal |
| Diffuse glomerulosclerosis | |
| Nodular glomerulosclerosis (Kimmelstiel-Wilson disease) | |
| Urinary infections | |
| Acute pyelonephritis | |
| Failure | |
| Necrotizing papillitis | |
| Emphysematous pyelonephritis | |
| Glycogen nephrosis (Armanni-Ebstein lesion) | |

Eye

| | |
|---|---|
| Retinopathy | Visual |
| Nonproliferative retinopathy; capillary Microaneurysms, retinal edema exudates, and hemorrhages | |
| Proliferative retinopathy: proliferation of small vessels, Failure | |
| hemorrhage fibrosis, retinal detachment | |
| Cataracts | |
| Transient refractive errors due to osmotic changes in lens | |
| Glaucoma due to proliferation of | |

TABLE 1-continued

Pathological Conditions Associated with Diabetes vessels in the iris
Infections

Nervous System

Cerebrovascular atherosclerotic disease: strokes, death
Peripheral neuropathy; peripheral sensory and motor cranial, autonomic Skin Infections: folliculitis leading to carbuncles
Necrobiosis lipoidica diabeticorum: due to microangiopathy
Xanthomas: secondary to hyperlipidemia
Cardiovasular system Coronary atherosclerosis: myocardial infarction, death
Peripheral atherosclerosis: limb ischemia, gangrene Reproductive system Increased fetal death rate (placental disease, neonatal respiratory distress syndrome, infection)

General

Increased susceptibility to infection
Delayed wound healing

Additional complications also include, for example, a general increased susceptibility to infection and wound healing. The term "treating" is also intended to include an increase in the average life expectancy of a diabetic individual compared to a non-treated individual. Other pathological conditions, chronic complications or phenotypic manifestations of the disease are known to those skilled in the art and can similarly be used as a measure of treating diabetes so long as there is a reduction in the severity of the condition, complication or manifestation associated with the disease.

As used herein, the term "preventing" is intended to mean a forestalling of a clinical symptom indicative of diabetes. Such forestalling includes, for example, the maintenance of normal levels of blood glucose in an individual at risk of developing diabetes prior to the development of overt symptoms of the disease or prior to diagnosis of the disease. Therefore, the term "preventing" includes the prophylactic treatment of individuals to guard them from the occurrence of diabetes. Preventing diabetes in an individual is also intended to include inhibiting or arresting the development of the disease. Inhibiting or arresting the development of the disease includes, for example, inhibiting or arresting the occurrence of abnormal glucose metabolism such as the failure to transfer glucose from the plasma into the cells. Therefore, effective prevention of diabetes would include maintenance of glucose homeostasis due to glucose-regulated insulin expression in an individual predisposed to a diabetic condition, for example, an obese individual or an individual with a family history of diabetes. Inhibiting or arresting the development of the disease also includes, for example, inhibiting or arresting the progression of one or more pathological conditions or chronic complications associated with diabetes. Examples of such pathological conditions associated with diabetes are listed in Table 1.

As used herein, the term "implanting" is intended to mean the introduction or transplantation of cells into an individual wherein the cells remain viable after implantation and maintain their glucose-regulated insulin secretion for at least one stimulation of glucose uptake. Implanting includes, for example, direct grafting of the cells, administration with other components such as matrix components, fragments or other molecules which facilitate adhesion of the cells. Implanting also includes cells grown on solid matrices or prosthetics as well as cells encapsulated in semi-permeable membranes or barriers. The term "implanting" is also intended to include the grafting of cells from non-solid tissues such as the hematopoietic system. Such implanting therefore includes, for example, the direct injection of cells into the blood stream, tissue or abdominal cavity of an individual or the introduction of the cells into an individual by surgical manipulation.

As used herein, the term "coexpressing" is intended to mean the expression of two or more molecules by the same cell. The coexpressed molecules can be polypeptides or nucleic acids. When referring to nucleic acids, the expression can be, for example, constitutive or inducible. Such nucleic acid sequences can also be expressed simultaneously or, alternatively, regulated independently. Various combinations of these modes of coexpression can additionally be used depending on the number and function of amino acid or nucleotide sequences being expressed. Those skilled in the art know, or can determine, what modes of coexpression can be used to achieve a particular goal or satisfy a desired need.

As used herein, the term "insulin" is used to mean a polypeptide capable of stimulating glucose uptake by cells in response to increased glucose levels. Insulin can correspond to the amino acid sequence or any portion thereof from a variety of vertebrate species such as human, porcine, equine, rat or bovine so long as the resulting expressed molecule retains at least one bioactive function such as the stimulation of glucose uptake, glycogen synthesis, amino acid uptake, or protein synthesis (see Table 2 below). The term also includes modified forms of insulin having amino acid substitutions that enhance or do not greatly diminish the bioactivity of the polypeptide to stimulate glucose uptake by cells. Insulin also can include additions or deletions of amino acid residues so long as it retains insulin bioactivity. A bioactive insulin can therefore have an activity that is similar to wild type insulin or is higher or lower than wild type insulin so long as the bioactive insulin stimulates glucose uptake by cells.

Generally, human insulin has the molecular weight of about 5.8 kDa. The human insulin A- and B-chain sequences are provided as exemplary sequences for the insulin polypeptides of the invention (see FIG. 4). The A-chain of human insulin corresponds to nucleotides 312–374 (SEQ ID NO:3) and amino acids 90–110 (SEQ ID NO:4), and the B-chain of human insulin corresponds to nucleotides 117–206 (SEQ ID NO:5) and amino acids 25–54 (SEQ ID NO:6) of the sequences shown in FIG. 4. Human insulin genomic DNA can be found at GenBank accession No. J00265, and human insulin cDNA can be found at GenBank accession No. X70508. Nucleotide and amino acid sequences of insulin polypeptides from species other than human are known to those skilled in the art. All of these sequences as well as substantial equivalents and functional fragments thereof that maintain insulin bioactivity are included within the term "insulin" as used herein. In general, insulin consists of an A-chain region disulfide linked to a B-chain region.

As used herein, the term "proinsulin" is intended to mean a precursor form of insulin. Proinsulin polypeptides of the invention can be the amino acid sequence, or portions thereof, corresponding to a variety of vertebrate species such as human, porcine, equine, rat or bovine so long as it contains an A- or B-chain region of insulin, or a functional fragment thereof. The term includes modified forms of proinsulin so long as the precursor polypeptide can be processed, or modified to be processed, into a bioactive form of insulin or into an A-chain or a B-chain region of insulin which is capable of assembling into a bioactive form of insulin. The precursor regions of the proinsulin polypeptides can be essentially any amino acid sequence so long as it does not negatively affect the processing of proinsulin into a bioactive form of insulin, an A-chain, a B-chain, or a functional fragment thereof. Therefore, the precursor region sequences can be, for example, the propeptide of insulin such as the proinsulin sequence shown in FIG. 4 or the C-chain region which are found in vertebrate proinsulin molecules. Alternatively, such precursor regions can be, for example, any of a variety of amino acid sequences, such as linker sequences, that are not normally found in vertebrate proinsulin molecules. The nucleotide and amino acid sequences of human proinsulin are recited as SEQ ID NOS:1 and 2, respectively, and are provided as exemplary sequences for the proinsulin polypeptides of the invention (see FIG. 4). Nucleotide and amino acid sequences of insulin polypeptides from species other than human are known to those skilled in the art. All of these sequences as well as substantial equivalents and functional fragments thereof, that maintain their ability to be processed into bioactive insulin or into an A-chain or a B-chain region of insulin which is capable of assembling into a bioactive form of insulin are included within the term as used herein. Proinsulin can consist, for example, of a C-chain connected to the B- and A-chain sequences.

As used herein, the term "proinsulin cleavage site" is intended to mean an amino acid sequence that can be recognized by a protease and cleaved, resulting in two or more amino acid fragments. A proinsulin cleavage site therefore includes, for example, a sequence within the proinsulin precursor molecule which, upon cleavage by a protease, converts the molecule into bioactive insulin or functional forms of an insulin A- or B-chain. The term similarly includes cleavage sites that are not derived from a wild type insulin sequence. For example, a cleavage site can be a sequence that is modified or altered so as to allow specific recognition and cleavage by a protease that would not naturally cleave a wild type proinsulin. Specific examples of proinsulin cleavage sites include tetrabasic amino acid sequences such as a Arg-Xaa-Lys/Arg/Xaa-Arg motif (SEQ ID NO:7), or dibasic amino acid sequences such as the Arg-Xaa-Lys/Arg-Arg (SEQ ID NO:8). Therefore, essentially any sequence can be used as a proinsulin cleavage site so long as it can be selectively recognized and cleaved by a protease.

As used herein, the term "protease" is intended to mean a polypeptide capable of specifically recognizing a proinsulin cleavage site and hydrolyzing a peptide bond. A protease therefore includes an endopeptidase that is capable of specifically recognizing a proinsulin cleavage site. A protease also includes the naturally occurring proinsulin cleaving endopeptidases known as PC3 (also known as PC1) and PC2, which normally reside in pancreatic islet β-cells. The term similarly includes other subtilisin related enzymes such as furin and PACE4 and the yeast endoprotease Kex 2. Other proteases with known and selective recognition sites are similarly included within the definition of the term.

As used herein, the term "glucose-regulated" is intended to mean the regulation of expression of a nucleic acid sequence by changes in levels of glucose. For example, glucose-regulated expression includes the induction of promoter activity by increased levels of glucose. Such glucose-regulated promoters include, for example, a TGF-α promoter element, a fibroblast growth factor promoter element, an insulin promoter element, a PC2 promoter element or a PC3 promoter element. The term "glucose" when used in reference to the regulated expression of a gene is intended to include both glucose and glucose metabolites so long as such metabolites can cause increased expression from a glucose-regulated promoter. A glucose metabolite includes those intermediate products of glucose metabolism such as glucose-6-phosphate, fructose-6-phosphate, glyceraldehyde-3-phosphate, glycerate-2-phosphate and pyruvate.

The term "glucose" when used in reference to glucose-regulated expression is also intended to include an intermediate or product of a biosynthetic pathway that is activated in response to increased levels of glucose and, therefore, increased glucose metabolism so long as such intermediates or products can cause increased expression from a glucose regulated promoter. Such a pathway includes, for example, the hexosamine biosynthetic pathway where glucosamine-6-phosphate is one intermediate which can activate a glucose regulated promoter. Other hexosamine biosynthetic pathway intermediates include, for example, glucosamine, N-acetyl glucosamine-6-phosphate, N-acetyl glucosamine-1-phosphate, UDP-N-acetyl glucosamine and other hexosamines. An intermediate or product of a metabolic pathway that is activated in response to increased levels of glucose is similarly included within the meaning of the term so long as such a metabolic intermediate or product can cause increased expression from a glucose regulated promoter.

As used herein, the term "pharmaceutically acceptable carrier" is intended to mean a solution or media which is appropriate for administration to an individual. Such solutions or media can act to maintain the stability of compounds and polypeptides and the viability of the cells. Pharmaceutically acceptable carriers are well known in the art and include aqueous solutions such as phosphate-buffered saline or media. A pharmaceutically acceptable carrier also includes additional compounds that act to enhance or increase the ability of the cells to attach or adhere to their in vivo environment. Such compounds can include, for example, extracellular matrix molecules such as fibronectin, collagen, laminin, proteoglycans, and fragments thereof containing cell adhesion binding sites.

As used herein, the term "selectable marker" is intended to mean a genotypic characteristic of a cell which can be used for identifying and isolating the cell. A selectable marker includes both endogenous genotypes as well as genotypes which are produced through the specific modification of a cell so long as they allow for the identification and isolation of the cell. Selectable markers are well known in the art and include, for example, expression of genes which allow for selection based on drug resistance, metabolite usage or affinity isolation methods. For example, an antibiotic resistance gene such as the neomycin phosphotransferase (neo) gene can be used as a selectable marker. Cells modified to contain and express the neo gene will be rendered resistant to antibiotic treatment, allowing for selection of these cells. The bacterial L-histidinol dehydrogenase (hisD) gene which confers resistance to the amino alcohol L-histidinol is also an additional example of a selectable marker. The hygromycin resistance gene is yet another specific example of a selectable marker. The selectable marker need not confer resistance to a particular treatment but can also be an expressed molecule that allows for selection of a cell by positive selection, such as with immunoaffinity beads.

As used herein, the term "prosthetic graft" is intended to mean cells seeded onto a biological material or contained within a semipermeable barrier that is suitable for implantation into an individual. Such a biological material is any substance which would allow for attachment of the cells and allow the cells to remain viable and functional within an individual. A prosthetic graft can consist of cells seeded onto a ring of polytetrafluoroethylene (PTFE) and then placed into an individual. Depending on the level of expression, cell populations greater than about $10^5$, preferably greater than about $10^6$, and more preferably greater than about $10^7$ or more cells grown on grafts can provide therapeutic benefit in vivo. A prosthetic graft can also consist of cells contained within a porous membrane or filter and then placed into an individual. A prosthetic graft can also include, for example, cells contained within a biological or synthetic matrix which can be implanted into an individual.

As used herein, the term "hexosamine synthetic pathway enzyme" is intended to mean a molecule which catalyzes the conversion of glucose or a glucose metabolite such as fructose-6-phosphate, to any one of the intermediates or products within the hexosamine biosynthetic pathway. For example, a converting enzyme of this pathway includes glutamine:fructose-6-phosphate amidotransferase (GFA), which catalyzes the conversion of fructose-6-phosphate to glucosamine-6-phosphate.

As used herein, the term "three-gene vector" is intended to mean a vector comprising elements sufficient to effect the expression of three nucleic acid sequences linked on a single vector. The nucleic acid sequences encoding the three genes can be transcribed as separate transcription units under the control of three separate promoters. The nucleic acid sequences encoding the three genes can also be transcribed as a single polycistronic transcription unit containing internal ribosome entry sites or as a polycistronic transcription unit containing two genes and a separate transcription unit encoding the third gene.

As used herein, the term "isolated" is intended to mean a population of cells which are substantially free of contaminants or material as they are normally found in nature. An isolated population of cells also includes cells that are a subpopulation of a larger group or type of cells. A "population" as used herein is intended to mean a group of two or more cells. The cells which make up the population can be of the same or different lineage and can be a homogenous or heterogenous group of cells.

The invention provides an isolated population of cells. The cells contain an expressible nucleic acid encoding proinsulin containing a proinsulin cleavage site. The cells also contain a glucose-regulated expressible nucleic acid encoding a protease that is capable of cleaving the proinsulin cleavage site to produce insulin.

Insulin is normally secreted by the pancreatic beta (β) islet cells. Mature insulin is derived from the processing of a precursor, proinsulin, in β islet cells. This conversion occurs in secretory vesicles and is the result of propeptide cleavage by endopeptidases.

The digestion of nutrients into glucose results in elevated blood glucose levels. Elevated blood glucose then stimulates insulin secretion by the pancreas, and insulin stimulates the uptake of glucose and its further metabolism for storage and fuel for use by tissues of the body. The expression of proinsulin processing enzymes is also regulated in response to elevated blood glucose. In diabetes, glucose homeostasis and metabolism is disrupted either directly at the level of insulin secretion or indirectly at the level of tissue responsiveness to insulin activity. Cells which normally secrete insulin can lose their ability to secrete a functional insulin peptide, or the biological responses to insulin secretion can be disrupted.

The invention is directed to coexpression of a glucose-regulated endoprotease and proinsulin, which results in secretion of bioactive insulin in response to elevated glucose levels and maintenance of glucose homeostasis by coupling insulin secretion with energy metabolism. The present invention provides cells that functionally mimic the normal process of glucose-regulated insulin secretion. Therefore, the cells of the invention provide a means of recoupling insulin expression and its activity to changes in levels of glucose. The cells can be used in therapeutic methods for the treatment of diabetes. Alternatively, the cells can be used in methods for the diagnosis and study of diabetes.

The cells of the invention are generated by introducing into the cells a vector comprising an expressible nucleic acid sequence encoding a proinsulin containing a proinsulin cleavage site and a glucose-regulated expressible nucleic acid encoding a protease capable of cleaving the proinsulin cleavage site. A proinsulin molecule containing a proinsulin cleavage site is one that contains a site which can be cleaved by a protease specifically recognizing the site and which, upon cleavage, results in a bioactive insulin molecule. The cells coexpress proinsulin and the cognate protease that recognizes the proinsulin cleavage site so that proinsulin is cleaved to form bioactive insulin.

A nucleic acid sequence of the invention that encodes proinsulin containing a proinsulin cleavage site can encode, for example, wild type proinsulin. Wild type bioactive insulin consists of an A-chain polypeptide that is disulfide linked to a B-chain polypeptide. The wild type proinsulin molecule contains a C-chain region located between the A- and B-chain regions that aids in the folding of the A- and B-chains for correct formation of the disulfide linkages. Wild type proinsulin contains two protease cleavage sites, one between the C- and A-chains and a second between the C- and B-chains. A nucleic acid sequence of the invention can therefore encode a wild type proinsulin that is cleaved into a bioactive insulin.

A bioactive insulin is a molecule that exhibits one or more of the well known activities associated with insulin action. Examples of the principle actions of insulin are shown in Table 2. A bioactive insulin of the invention exhibits one or more of the activities shown in Table 2, in particular, the activity of increasing glucose uptake.

TABLE 2

Principal Actions of Insulin.

Adipose tissue

1. Increased glucose entry
2. Increased fatty acid synthesis
3. Increased glycerol phosphate synthesis
4. Increased triglyceride deposition
5. Activation of lipoprotein lipase
6. Inhibition of hormone-sensitive lipase
7. Increased K$^+$uptake Muscle 1. Increased glucose entry
2. Increased glycogen synthesis
3. Increased amino acid uptake TABLE 2-continued Principal Actions of Insulin.

4. Increased protein synthesis in ribosomes
5. Decreased protein catabolism
6. Decreased release of gluconeogenic amino acids
7. Increased ketone uptake
8. Increased K$^+$uptake Liver 1. Decreased ketogenesis
2. Increased protein synthesis
3. Increased lipid synthesis
4. Decreased glucose output due to decreased gluconeogenesis and increased glycogen synthesis General 1. Increased cell growth The invention employs nucleic acids encoding proinsulin that can be cleaved into a bioactive insulin. When using a wild type proinsulin, the expressible nucleic acid of the invention contains the sequences corresponding to the A- and B-chains of insulin, directly linked in cis on a single vector and separated by a sequence encoding for a C-chain region. In this case, the proinsulin molecule can contain at least two cleavage sites, one between the C- and A-chains and a second between the C- and B-chains. However, additional cleavage sites within the C-chain could also be constructed, if desired, for example, to increase the efficiency of cleavage. Such a nucleic acid sequence encoding wild type insulin consists of a single, contiguous A-C-B chain sequence that is transcribed and translated as a single product and converted to bioactive insulin.

In addition to the arrangement of A, C and B chains as found in wild type proinsulin, the expressible nucleic acid sequence can also encode a proinsulin comprising an A and B chain separated by a linker sequence. As found in wild type insulin, a cleavage site is inserted between the A chain and the linker and the B chain and the linker so that, upon expression of the appropriate protease, the proinsulin is cleaved into A- and B-chains that can associate to form a bioactive insulin. The linker sequence can be, for example, a size that facilitates correct pairing of the disulfide bonds that connect the A- and B-chains of insulin. The linker sequence can also be as small as a single cleavage site that separates the A- and B-chains and that, upon cleavage with a protease, releases the A- and B-chains for assembly into active insulin.

The proinsulin of the invention can be from a variety of vertebrate species and can be a portion of a proinsulin sequence so long as the translated nucleotide sequence can be processed into an insulin molecule that stimulates glucose uptake by a cell. The insulin molecule is processed, for example, by cleavage at a proinsulin cleavage site that releases an A- and B-chain so that they form an active insulin molecule. A proinsulin cleavage site can be in any region of the proinsulin molecule so long as cleavage at that site will not abolish the activity of the resulting insulin molecule.

An expressible nucleic acid encoding proinsulin containing a proinsulin cleavage site can be constructed using methods well known in the art. An exemplary expressible nucleic acid sequence encoding proinsulin containing a proinsulin cleavage site is provided herein as SEQ ID NO:2. Methods for constructing an expressible nucleic acid sequence are known in the art, for example, as described by Sambrook et al. (*Molecular Cloning: A Laboratory Manual*, Cold Spring Harbor Laboratory Press, Cold Spring Harbor (1989)) and Ausubel et al. (*Current Protocols in Molecular Biology*, John Wiley & Sons, New York (1998)). For example, a nucleic acid sequence encoding proinsulin containing a proinsulin cleavage site can be obtained using polymerase chain reaction. A tissue or cell line from the appropriate organism can be used to amplify insulin or proinsulin sequences. Once a proinsulin sequence has been obtained, the native cleavage site can be used. Alternatively, a cleavage site can be inserted at the appropriate position in the sequence, for example, using site-directed mutagenesis as described below.

Insulin is secreted by pancreatic β cells to regulate glucose levels and is directed to the secretory pathway by a signal sequence. The proinsulin of the invention similarly has an appropriate signal sequence for directing proinsulin to the secretory pathway. The signal sequence can be a signal sequence found in wild type insulin or can be any signal sequence that directs proinsulin to the secretory pathway. Appropriate signal sequences sufficient to direct proinsulin to the secretory pathway are well known in the art and can be derived from essentially any protein that is processed in the secretory pathway.

The above-described proinsulin molecules are expressed as a single transcription and translation unit, which is cleaved to produce insulin. However, the invention also provides a proinsulin where the A- and B-chains are expressed as separate transcription units. When expressed as separate transcription units, the translation product of both the A- and B-chains contains signal sequences sufficient to direct the A- and B-chains to the secretory pathway. For example, the translation product of the separately expressed A- and B-chains can each have a signal sequence for directing the A- and B-chains to the secretory pathway so that the A- and B-chains can associate to form a bioactive insulin. The separate transcription units for the A- and B-chains can encode a translation product containing a protease cleavage site that, upon cleavage, releases the A- and B-chains. However, when expressed as separate transcription units, the proinsulin translation products need not contain a proinsulin cleavage site. Instead, the translation products of the transcription units can directly associate into a bioactive insulin. Expression of A- and B-chains as separate transcription units can be useful in the invention even though the formation of bioactive insulin is less efficient than that of proinsulin cleaved by a protease so long as a sufficient level of bioactive insulin is formed to mediate the desired effect of regulating the level of glucose.

The separate A- and B-chain transcription units can be encoded on the same expression vector or can be encoded on separate expression vectors. Separate expression vectors can be used where each vector contains a portion of the proinsulin encoding sequence so long as coexpression of the A- and B-chains encoded by the vectors results in assembly of the A- and B-chains into a bioactive insulin. For example, two expression vectors can be used, each containing a nucleic acid sequence encoding either the A- or B-chain of insulin.

Nucleic acids encoding proinsulin containing a proinsulin cleavage site require coexpression of a corresponding protease that recognizes the proinsulin cleavage site. In normal individuals, processing of bioactive insulin from wild type proinsulin occurs in the secretory pathway of β cells. Therefore, wild type proinsulin or proinsulin containing a wild type proinsulin cleavage site expressed in a β cell can be cleaved by the native endopeptidases PC1, PC2 and PC3.

However, other cell types are also capable of processing molecules through the secretory pathway. For example, a nucleic acid encoding proinsulin containing a proinsulin cleavage site can be introduced into a non-β cell of the desired cell type that has secretory pathway processing machinery. In this case, the proinsulin cleavage site is engineered to be recognized by an endogenous protease in the cell, allowing cleavage of proinsulin by a protease expressed endogenously in the cell.

Alternatively, instead of using endogenous proteases, coexpression of a protease with a nucleic acid encoding proinsulin containing a proinsulin cleavage site can be achieved by introducing an exogenous protease into the cell. For example, an exogenous protease can be introduced into a cell using an expression vector that is co-transfected or separately transfected with an expression vector containing a nucleic acid encoding proinsulin containing a proinsulin cleavage site. Expression of an exogenous protease can be advantageous in that, instead of relying on the activity of an endogenous protease, a variety of sequence specific proteases can be coexpressed with a proinsulin containing the corresponding cleavage site. Various proteases and methods for introducing corresponding cleavage sites are described below.

The coexpression of proinsulin and the protease can be achieved using a variety of expression vectors. The proinsulin and the protease can be expressed on the same expression vector or on separate expression vectors so long as coexpression of proinsulin and the protease encoding sequences results in expression of a protease that is capable of cleaving the proinsulin into a bioactive insulin molecule in response to increased levels of blood glucose.

The coexpression of proinsulin and protease need not be co-regulated at the transcriptional level so long as the protease and proinsulin polypeptides are coexpressed so that the protease can cleave proinsulin into peptides that can associate to form a bioactive insulin. Coexpression can be the result of inducible expression of one or both encoding sequences or constitutive expression of one or both sequences or combinations thereof. For example, proinsulin can be constitutively expressed while the protease is expressed under glucose regulation. The fibronectin promoter element is one example of a constitutive promoter that can maintain expression of proinsulin over a sustained period of time. By expressing a molecule constitutively, the time for responding to increased glucose levels is dependent on the synthesis of only one molecule rather than two, resulting in a more rapid response. Furthermore, by having either protease or proinsulin expression responsive to glucose, the amount of bioactive insulin produced is regulated by the level of glucose.

The methods of the invention generally employ vectors containing a nucleic acid encoding a glucose-regulated protease. However, a vector of the invention can comprise a glucose-regulated proinsulin and a constitutively expressed protease. In addition, if proinsulin A- and B-chains are expressed as separate transcription units and the translation products lack a protease cleavage site, the proinsulin gene can be controlled by a glucose-regulated promoter. Regardless of which expression element is glucose regulated or constitutively expressed, the resultant translation product is capable of forming bioactive insulin that is regulated by glucose levels.

Glucose-regulated expression of a molecule of interest such as a protease can be achieved using a variety of promoter elements that control expression of a downstream gene in response to changes in levels of glucose. Elements that are responsive to glucose are inducible in that they generally exhibit low activity in the absence of glucose and are up-regulated in the presence of increased glucose. For example, it is known that TGF-α promoter activity is responsive to glucose (McClain et al., *Proc. Natl. Acad. Sci. USA* 89:8150–8154 (1992); and Raja et al., *Mol. Endocrinol.* 5:514–420 (1991)). Also, sequences from other glucose-responsive promoter elements can be used such as promoter elements from wild-type insulin, fibroblast growth factor (FGF), epidermal growth factor (EGF), PC2 or PC3 genes (Sander et al., *Proc. Natl. Acad. Sci. USA* 95:11572–11577 (1998)). Other glucose responsive promoter elements can be found, for example, in genes for acetyl-CoA carboxylase, 6-phosphofructo-2-kinase, and L-type 15 pyruvate kinase (Zhang and Kim, *Arch. Biochem. Biophys.* 15:227–232 (1997); Dupriez and Rousseau, *DNA Cell Biol.* 16:1075–1085 (1997); Antoine et al., *J. Biol. Chem.* 272:17937–17943 (1997); and Kennedy et al., *J. Biol. Chem.* 272:20636–20640 (1997)).

To generate a glucose-regulated expressible nucleic acid encoding a protease, the entire promoter sequence can be inserted immediately 5' of the protease sequence in an expression vector. Alternatively, a sequence corresponding to a portion of the glucose-responsive promoter sequence can be used so long as the chosen region contains at least the minimal sequences sufficient for glucose-regulated stimulation of transcriptional activity. A nucleic acid encoding a protease under glucose-regulation can be constructed using methods well known in the art as described, for example, by Daniels et al. (*Mol. Endocrinol.* 7:1041–1048, (1993)).

Additional glucose-regulated promoter or enhancer elements suitable for use in the invention can be identified and tested using methods well known in the art and current information available regarding activity of known promoter elements. Specific sequences responsible for glucose induced activation of gene transcription by the insulin promoter have been mapped and methods for the identification of such sequences are described by Odagiri et al. *J. Biol. Chem.*, 271:1909–1915 (1996). Additionally, elements from other promoter sequences that are inducible by glucose can be used.

To identify additional glucose-regulated promoter elements, a sequence corresponding to the glucose-responsive region of a promoter can be linked 5' to a reporter sequence. Luciferase or β-galactosidase are exemplary reporter gene sequences that can be used. Glucose-responsive induction of the promoter element can be confirmed in vitro using cells that have been modified to express the test promoter/reporter gene sequence. Promoter elements that are glucose-responsive will result in a higher level of detectable reporter gene product, for example, luciferase or β-galactosidase, in cells cultured in the presence of high glucose with low or no expression in low glucose. Promoter elements with altered activity such as enhanced activity in response to changes in glucose can also be identified by using such a reporter system. New glucose-responsive promoter elements can be identified by testing the ability of the element to direct increased expression of a reporter gene in response to increased or high levels of glucose. Elements identified as glucose-responsive can then be used to regulate insulin expression in a glucose-regulated manner.

It is understood that a glucose-regulated promoter is one that is responsive to increased glucose levels as a positive regulator of operationally linked downstream genes. The glucose-regulated promoter of the invention is responsive to increased glucose levels or to increased levels of metabolites that result from increased glucose levels. A glucose-regulated promoter useful in the invention can therefore be responsive to a metabolite of glucose that is positively correlated with the level of glucose. Regardless of the mechanism of regulation of a glucose responsive promoter, a promoter is considered to be a glucose-regulated promoter if it increases expression of downstream genes in response to increased glucose levels.

In addition to the use of a glucose-regulated promoter to control expression of an operationally linked gene, the invention is also directed to the use of additional mechanisms to enhance the production of glucose-responsive bioactive insulin. Increases in glucose levels lead to a variety of physiological responses that result in production of numerous metabolic products. Since the invention is directed to increasing insulin in a glucose-dependent manner, any metabolic product that is correlated with increased levels of glucose can be used as a sensor for increases in glucose levels. In addition, these metabolic products can also be used to enhance the sensitivity to glucose when combined with a glucose-regulated promoter.

For example, enzymes in the hexosamine synthetic pathway catalyze the conversion of glucose or a glucose metabolite such as fructose-6-phosphate, to any one of the intermediates or products within the hexosamine biosynthetic pathway. One converting enzyme of this pathway is glutamine:fructose-6-P amidotransferase (GFA), which catalyzes the conversion of fructose-6-phosphate to glucosamine-6-phosphate. Because the hexosamine synthetic pathway is stimulated by glucose due to increased availability of substrate, the activity of enzymes in this pathway such as GFA can be used to increase sensitivity to glucose. For example, glucosamine, the product of the hexosamine synthetic pathway enzyme GFA, was shown to be a stronger inducer of TGFα promoter activity than glucose (Daniels et al., *Mol. Endocrinol.* 7:1041–1048 (1993); McClain et al., *Proc. Natl. Acad. Sci. USA* 89:8150–8154 (1992); Raja et al., *Mol. Endocrinol.* 5:514–520 (1991)). Therefore, expression of a hexosamine synthetic pathway enzyme such as GFA can be used to increase the activity of a glucose-regulated promoter such as the TGFα promoter. However, it is understood that any activity associated with glucose levels, including enzymatic activity of a glucose metabolic pathway, can be used in methods and cells of the invention to sense glucose or enhance the response to glucose.

The invention additionally provides a population of cells comprising an expressible nucleic acid encoding proinsulin containing a proinsulin cleavage site, a glucose-regulated expressible nucleic acid encoding a protease and a hexosamine biosynthetic pathway enzyme. For example, the invention provides an isolated population of cells expressing proinsulin, a glucose-regulated protease, and glutamine:fructose-6-phosphate amidotransferase (GFA). Such cells have enhanced sensitivity to glucose levels due to increased glucosamine levels in response to increased glucose levels. Increased glucosamine levels further activate the glucose-regulated promoter controlling protease expression. Such cells can be advantageously used to provide glucose-dependent insulin expression in a diabetic patient.

The methods of the invention are directed to treating or preventing diabetes in an individual by providing to the individual a supply of insulin that is responsive to the level of glucose. In one embodiment, glucose regulated expression of bioactive insulin is achieved using a glucose-regulated promoter. However, the methods of the invention can also utilize an expression vector that is inducible by a molecule that is coordinated with glucose levels. In an individual, glucose levels increase upon ingestion of food. Therefore, administration of a molecule at about the same time as ingestion of food results in correlation of levels of the molecule with increases in glucose levels.

For example, a promoter element can be an element that is inducible by mechanisms other than glucose or by a regulating molecule that is not glucose or a glucose metabolite. Glucose-regulated induction of such an element can be achieved by administering to an individual the regulating molecule at a specific time before, during or following ingestion of a meal. For example, a promoter element controlling a protease encoding nucleic acid sequence can be activated by the administration or ingestion of a molecule which specifically activates that promoter element. The molecule can be formulated into a drug form for easy absorption by the intestinal mucosa. The amount and timing of administration of the molecule can be readily determined by one skilled in the art by measuring the absorption of the molecule relative to increases in glucose upon ingestion of food. Glucose-regulated expression of insulin is then achieved by administration of the drug with a meal or at a time before or after the meal that allows levels of the molecule to be correlated with glucose levels.

As described above, methods of the invention employing proinsulin containing a proinsulin cleavage site require coexpression of a protease. A variety of proteases can be selected for use in the invention so long as the protease is able to recognize and specifically cleave a proinsulin cleavage site in the expression vector and generate bioactive insulin. Many bioactive forms of proteins are produced from precursor molecules by endoproteolysis. For example, active forms of molecules such as melanocyte stimulating hormone, insulin-like growth factors I and II, adrenocorticotropic hormone, β-endorphin, enkephalin and glucagon are all produced by cleavage with a protease at a specific cleavage site. The specific proteases which convert these described molecules can also be used as a protease of the invention. Other proteases can also be selected for use in the invention if it is capable of recognizing and cleaving at a proinsulin cleavage site.

The proteases of the invention will generally be endopeptidases having specificity for a peptide sequence rather than recognition of a single amino acid as a cleavage site. As described above, examples of proteases useful in the invention include PC1, PC2, PC3, furin, PACE4 and Kex2. Other proteases useful in the invention include enterokinase, which recognizes the sequence Asp-Asp-Asp-Asp-Lys (SEQ ID NO:9) and cleaves after Lys, or factor Xa, which recognizes the sequence Ile-Glu-Gly-Arg (SEQ ID NO:10) and cleaves after R. When using proteases that do not recognize the native proinsulin cleavage site are used, the proinsulin cleavage site is modified to the cognate recognition site for the protease so that the site can be cleaved by the protease. Essentially any protease with specificity that allows cleavage of a proinsulin cleavage site while retaining biological function of the cleaved proinsulin products can be used in the invention. As described above, methods for isolating protease genes are well known in the art (Sambrook et al., supra (1989) and Ausubel et al. supra (1998)).

The protease is coexpressed with proinsulin, and, because proinsulin is targeted to the secretory pathway, the protease is similarly targeted to the secretory pathway. Therefore, the protease gene product encoded by the vectors of the invention has a signal sequence for targeting the protease to the secretory pathway so that proinsulin can be cleaved by the protease. As with proinsulin, any signal sequence that directs the protease to the secretory pathway can be used.

Just as a variety of proteases can be selected for use in the invention, a variety of proinsulin cleavage sites can be selected for insertion into a proinsulin molecule. A proinsulin cleavage site can be any sequence that is recognized and specifically cleaved by a protease. Selection of a proinsulin cleavage site sequence will depend on the protease that is used and can be determined by one skilled in the art.

Proteases can differ in their efficiency of cleavage at a particular sequence. Therefore, selection of a cleavage site will also depend on the level of specificity and cleavage desired. For example, cleavage of the prohormone pro-nerve growth factor to the mature form is catalyzed by furin at dibasic sites such as Arg-Arg in the regulated pathway of endocrine cells. However, the endoprotease furin can also cleave with high efficiency at tetrabasic amino acid sequences recited as SEQ ID NOS:7 and 8. Furin also cleaves at other tetrabasic amino acid sequences but with lower efficiency. Therefore, any one of the above dibasic or tetrabasic sites can be inserted into a proinsulin molecule and used as a protease cleavage site for a protease such as furin.

The location of a cleavage site in proinsulin depends on the particular arrangement of proinsulin elements in the expressible nucleic acid encoding proinsulin. For example, the cleavage site can be outside or within the A- and B-chain regions so long as the cleaved proinsulin can associate to form bioactive insulin that can stimulate glucose uptake. In a nucleic acid sequence encoding proinsulin elements such as the A- and B-chains, various arrangements of elements can be used for expressing a proinsulin containing a cleavage site. For example, the number of cleavage sites contained in the proinsulin molecule can vary depending on the particular combination of encoding nucleic acid sequences used for expressing proinsulin, but will generally be at least one cleavage site, but can be two, three or more cleavages sites.

A single cleavage site can be used, for example, if an A- and B-chain are separated by a linker containing a single cleavage site. Alternatively, a single cleavage site can be used, for example, if the nucleic acid sequence encodes insulin with an inhibitory sequence that is cleaved to release bioactive insulin. A single cleavage site can be useful in the invention even though the formation of bioactive insulin is less efficient than that of proinsulin with two cleavage sites so long as a sufficient level of bioactive insulin is formed to mediate the desired effect of regulating the level of glucose.

A proinsulin containing two cleavage sites can be used, for example, when proinsulin elements are arranged as in wild type proinsulin such as A-C-B or as in a proinsulin of the structure A-linker-B as described above. The choice of a particular combination of encoding nucleic acid sequences depends on the particular insulin encoding sequence chosen, the protease chosen, the efficiency with which the protease cleaves the proinsulin cleavage site, the efficiency of the nucleic acid sequence for encoding a correctly transcribed and translated product and the efficiency of folding of the cleaved molecule into a bioactive insulin. Furthermore, the combination of nucleic acid sequences and the number of cleavage sites used can depend on the cell type chosen, particular need or use of the modified cells or ease of construction of the encoding sequence. These determinations can readily be made by one skilled in the art.

As described above, proteases and cleavage sites specifically recognized by the proteases are well known in the art and a skilled artisan would know the appropriate methods to use to modify a nucleic acid to contain such a sequence and test for efficacy of the protease for the cleavage site. Modification of a nucleic acid sequence to contain a proinsulin cleavage site can be performed by standard molecular biology techniques known in the art as described, for example, by Sambrook et al., supra (1989) and Ausubel et al. supra (1998). For example, a specific proinsulin cleavage site can be constructed using polymerase chain reaction and cleavage site sequence-specific primers to generate a proinsulin cleavage site. Verification that the modified site is cleaved by the protease can then be performed in vitro using the protease, appropriate buffers and a sufficient quantity of isolated translation product of the proinsulin sequence. Detection of peptide fragments of appropriate size based on the known location of the cleavage site within the proinsulin sequence can be used to confirm the efficacy of the protease for the cleavage site.

For example, a proinsulin cleavage site recognized by furin can be introduced into proinsulin. Sequence-specific primers that correspond to the tetrabasic furin recognition sequence Arg-Xaa-Lys-Arg (SEQ ID NO:ll) or any other specific recognition sequence can be introduced into proinsulin. The cleavage site can be inserted, for example, at the B-C and C-A junctions corresponding to wild-type proinsulin nucleic acid sequence as described by Groskreutz et al. (*J. Biol. Chem.,* 269:6241–6245 (1994)) to produce a proinsulin molecule that contains a proinsulin cleavage site.

The vectors of the invention comprising an expressible nucleic acid encoding proinsulin containing a proinsulin cleavage site and a glucose-regulated protease can be prepared by a variety of methods well known to those skilled in the art. The vectors contain transcriptional regulatory elements that allow expression in the cell type selected for implantation. For example, the vectors contain constitutive or inducible promoters such as a glucose-regulated promoter operationally linked, for example, to a protease so that a glucose-regulated protease is expressed in the cell to effect proinsulin cleavage. Additionally, the vector can encode for proteins that enhance responsiveness to glucose levels such as a hexosamine biosynthetic pathway enzyme. Expression vectors of the invention can also contain tissue specific regulatory elements such as enhancers that allow for targeted expression in specific tissues.

A vector of the invention can also contain a selectable marker. A variety of selectable markers are well known to those skilled in the art (Sambrook et al., supra (1989); Ausubel et al. supra (1998)). For example, the neo gene that encodes for neomycin resistance can be encoded by a vector of the invention. Other selectable markers include hisD and the hygromycin resistance gene.

As described above, a single vector can encode the expression elements or the expression elements can be encoded on separate vectors. If it is desired to express two or more elements, the individual elements can be expressed from the same vector or on separate vectors, or any combination of vectors containing one to all of the desired expression elements. For example, a single expression vector can express four independent expression elements such as proinsulin, a protease, glutamine-6-phosphate amidotransferase, and a selectable marker. Alternatively, each of these four independent expression elements can be expressed on four separate vectors. Although expression elements can be encoded by separate vectors, the combination of expression elements into a single expression vector can be advantageous in that only a single vector need be introduced into a cell.

Vectors of the invention can be plasmid or viral based vectors. In the case of a viral vector, the vector can contain, for example, at least one viral long terminal repeat and a promoter sequence upstream of and operably linked to a nucleotide sequence encoding the gene product of interest, followed by at least one viral long terminal repeat and polyadenylation signal downstream of the sequence encoding the gene product of interest. In the case of a single vector encoding for more than one gene of interest, each gene of interest can be expressed as separate transcription units. Alternatively, multiple genes can be transcribed as a single transcription unit that contains internal ribosome entry sites that allow expression of the genes from a polycistronic messenger RNA (Adam et al., *J. Virol.* 65:4985–4990 (1991)). Additional nucleic acid sequences can be inserted into the vector using methods well known in the art.

Representative retroviral vectors suitable for use in the invention and methods for their design are described for example, in Osborne and Miller, *Proc. Natl. Acad. Sci. USA,* 85:6851–6855 (1988); Osborne et al., *Proc. Natl. Acad. Sci. USA.* 92:8055–8058 (1995); Ramesh et al., *Nuc. Acids. Res.,* 24:2697–2700 (1996); and Hock et al., *Blood.* 74:876–881 (1989). Other vectors may also be used and are well known in the art, such as lentiviral vectors, DNA vectors, adenoviral vectors, pseudotype retroviral vectors, Epstein-Barr viral vectors, adeno-associated virus, vesicular stomatitis virus-g (VSV-g), VL30 vectors, and liposome mediated vectors.

In one embodiment, a vector of the invention comprises a nucleic acid sequence encoding a modified human proinsulin containing a furin cleavage site (Bell et al., *Nature* 282:525–527 (1979); Sures et al., *Science* 208:57–59 (1980); Chekhranova et al., *Mol. Biol.* 26:596–600 (1992)), a nucleic acid sequence for the protease furin (Creemers et al., *Mol. Biol.,* 11:127–138 (1992)) under the control of a glucose-responsive promoter element from the TGF-α gene (McClain et al., supra (1992); and Raja et al., supra (1991)) and a nucleic acid sequence for a selectable marker such as the neo gene.

An example of a vector that allows further enhancement of glucose-regulated insulin expression is a vector encoding glutamine:fructose-6-phosphate amidotransferase cDNA (Sayeski et al., *Gene,* 140:289–290 (1994)). Such a vector can be used to enhance insulin expression by co-transfecting the vector with a vector containing a glucose-regulated promoter, resulting in a stronger induction of a gene operationally linked to a glucose-regulated promoter element.

Once an expression vector comprising an expressible nucleic acid encoding proinsulin containing a proinsulin cleavage site and a glucose-regulated protease has been constructed, the vector can be verified for expression of a proinsulin molecule that is cleaved and assembled into insulin using methods well known in the art. For example, the sequence can be introduced into a cell that does not express insulin and the culture media assayed for the presence of mature insulin using an assay such as ELISA or radioimmunoassay (RIA). Alternatively, the expressed product can be tested for its ability to induce any one of the principal actions of insulin such as those listed in Table 2. For example, the expressed product can be tested for its ability to stimulate increased transfer of glucose into cultured adipocytes or muscle cells. Measurement of the amount of transfer into the cells can be made by using radiolabelled glucose. Alternatively, the expressed product can be tested for insulin bioactivity by assessment of increased uptake of a radiolabelled amino acid by cultured muscle cells.

The invention provides a cell or population of cells comprising an expressible nucleic acid encoding proinsulin containing a proinsulin cleavage site and a glucose-regulated expressible nucleic acid encoding a protease capable of cleaving the proinsulin cleavage site to produce insulin. A cell or an isolated population of cells of the present invention includes, for example, a cell or population of cells that normally do not produce insulin such as non-β islet cells and that are modified to express and secrete insulin. The cells are engineered to express a protease that is regulated in response to changes in glucose levels so that the modified cells functionally mimic glucose-regulated insulin secretion in β islet cells. Moreover, glucose-regulated expression of the protease advantageously results in the amplification of insulin expression over levels of insulin expression that would be expected from coexpression of the protease without glucose-regulation. The cells are modified so as to coexpress both a precursor form of insulin, or proinsulin, and a protease which effects the cleavage of the precursor into functional subunits that can associate to form bioactive insulin.

Numerous different types of cells can be used to construct modified cells which functionally mimic glucose-regulated insulin secretion. Cell types to be selected for generating the modified cells of the invention are those which are capable of polypeptide synthesis and secretion. With the exception of highly specialized cell types, the large majority of cells meet these criteria. For example, red blood cells which are terminally differentiated cells, have lost their protein synthesis ability and are therefore unlikely candidates for the insulin secreting cells of the invention. However, with the exclusion of the few cell types that cannot synthesize and secrete a polypeptide such as those characterized above, essentially all other cell types can be used for constructing the modified cell or cell populations of the invention. The actual cell type to be used will, therefore, depend on the intended use of the modified cells by those skilled in the art.

The cell type chosen for modification is selected according to the biological characteristics of the cell and according to gene expression criteria well known in the art. For example, objective criteria such as the ease of culture efficiency, the ease of genetic modification and other routine cellular and molecular manipulations can be used to evaluate and select the cell type for modification. Those cell types which can be passaged for several generations without substantial loss in viability are preferable candidates for modification to glucose-regulated insulin producers. As will be described further below, such cell types include, for example, both primary cells as well as cell lines. Additionally, criteria such as the proliferation characteristics can also be evaluated for selection of the cell type to be modified.

Cell types are additionally selected according the efficiency with which they can be modified to express proinsulin and a glucose-regulated protease of the invention. Cell types that can be readily modified and selected for the expression of the introduced genes by any of a variety of methods known in the art are applicable for constructing the glucose-regulated insulin producing cells of the invention. Availability of promoter and regulatory elements can also be included as a criteria for selecting a particular cell type for modification. Such characteristics and criteria are routine and well know to those skilled in the art.

Various combinations of the above exemplary characteristics as well as other characteristics can additionally be used for selecting a cell type to modify. For example, if the objective is to achieve a particular level of insulin expression using a relatively small number of cells, then a cell type which is efficiently modified and can express high levels of glucose-regulated insulin can be selected to achieve the desired result. In contrast, if cell number is not a limiting factor, then it can be desirable to select the cell type because of favorable growth or proliferation characteristics. Additionally, various expression elements can be utilized to augment or modulate the level of proinsulin and protease expression so as to complement advantageous characteristics or overcome any deficiencies of the selected cell types for modifications. Such criteria and characteristics are well known or can be determined by those skilled in the art.

For therapeutic applications, the above cell populations can additionally be chosen to be implantable in an individual and remain viable in vivo without being substantially rejected by the host immune system. Those skilled in the art know what characteristics should be exhibited by cells to remain viable following implantation. Moreover, methods well known in the art are available to augment the viability of cells following implantation into a recipient individual.

One characteristic that can be exhibited by the cell or cell population to be implanted is that they are substantially immunologically compatible with the recipient individual. A cell is immunologically compatible if it is either histocompatible with recipient host antigens or if it exhibits sufficient similarity in cell surface antigens so as not to elicit an effective host anti-graft immune response. Specific examples of immunologically compatible cells include autologous cells isolated from a diabetic individual and allogeneic cells which have substantially matched major histocompatibility (MHC) or transplantation antigens with the recipient individual. Immunological compatibility can be determined by antigen typing using methods well known in the art. Using such antigen typing methods, those skilled in the art will know or can determine what level of antigen similarity is necessary for a cell or cell population to be immunologically compatible with a recipient individual. The tolerable differences between a donor cell and a recipient can vary with different tissues and can be readily determined by those skilled in the art.

In addition to selecting cells which exhibit characteristics that maintain viability following implantation into a recipient individual, methods well known in the art can be used to reduce the severity of an anti-graft immune response. Such methods can therefore be used to further increase the in vivo viability of immunologically compatible cells or to allow the in vivo viability of less than perfectly matched cells or of non-immunologically compatible cells. Therefore, for therapeutic applications, it is not necessary to select a cell type from the diabetic individual to achieve viability of the modified cell following implantation. Instead, and as described further below, alternative methods can be employed which can be used in conjunction with essentially any donor cell to confer sufficient viability of the modified cells to achieve a particular therapeutic effect.

For example, in the case of partially matched or non-matched cells, immunosuppressive agents can be used to render the host immune system tolerable to engraftment of the implanted cells. The regimen and type of immunosuppressive agent to be administered will depend on the degree of MHC similarity between the modified donor cell and the recipient. Those skilled in the art know, or can determine, what level of histocompatibility between donor and recipient antigens is applicable for use with one or more immunosuppressive agents. Following standard clinical protocols, administration and dosing of such immunosuppressive agents can be adjusted to improve efficiency of engraftment and the viability of the cells of the invention. Specific examples of immunosuppressive agents useful for reducing a host anti-graft immune response include, for example, cyclosporin, corticosteroids, and the immunosuppressive antibody known in the art as OKT3.

Another method which can be used to confer sufficient viability on partially-matched or non-matched cells is through the masking of the cells or of one or more MHC antigen(s) to protect the cells from host immune surveillance. Such methods allow the use of non-autologous cells in an individual. Methods for masking cells or MHC molecules are well known in the art and include, for example, physically protecting or concealing the cells, as well as disguising them, from host immune surveillance. Physically protecting the cells can be achieved, for example, by encapsulating the cells within a semi-permeable barrier that allows exchange of nutrients and macro molecules. Such a barrier prevents contact of host immune cells such as T-cells with the cells contained within the semi-permeable barrier but still allows glucose-regulated induction and secretion of insulin into the circulation system. Encapsulated cells can therefore be used as an implantable device for providing viable insulin producing cells which are glucose-regulated. The encapsulated cells can be permanently implanted or periodically replaced depending on the cell type used and the location where the device is implanted. An example of a semi-permeable barrier includes natural or synthetic membranes with a pore size that excludes cell-cell contact. Generally, a pore size of about 0.22 mm is sufficient to allow exchange of macromolecules such as insulin and growth factors without allowing immune cells access to implanted cells. However, other pore sizes can also be used without affecting viability of the glucose-regulated insulin producing cells. Alternatively, antigens can be disguised by treating them with binding molecules such as antibodies that mask surface antigens and prevent recognition by the immune system.

Immunologically naive cells can also be used for constructing glucose-regulated insulin producing cells. Immunologically naive cells are devoid of MHC antigens that are recognized by a host anti-graft immune response. Alternatively, such cells can contain one or more antigens in a non-recognizable form or can contain modified antigens that faithfully mirror a broad spectrum of MHC antigens and are therefore recognized as self-antigens by most MHC molecules. The use of immunologically naive cells therefore has the added advantages of circumventing the use of the above-described immunosuppressive methods for augmenting or conferring immunocompatibility onto partially or non-matched cells. As with autologous or allogeneic cells, such immunosuppressive methods can nevertheless be used in conjunction with immunologically naive cells to facilitate viability of the glucose-regulated insulin producing cells.

An immunologically naive cell, or broad spectrum donor cell, can be obtained from a variety of undifferentiated tissue sources, as well as from immunologically privileged tissues. Undifferentiated tissue sources include, for example, cells obtained from embryonic and fetal tissues. An additional source of immunologically naive cells include stem cells and lineage-specific progenitor cells. These cells are capable of further differentiation to give rise to multiple different cell types. Stem cells can be obtained from embryonic, fetal and adult tissues using methods well known to those skilled in the art. Such cells can be used directly or modified further to enhance their donor spectrum of activity.

Immunologically privileged tissue sources include those tissues which express, for example, alternative MHC antigens or immunosuppressive molecules. A specific example of alternative MHC antigens are those expressed by placental cells which prevent maternal anti-fetal immune responses. Additionally, placental cells are also known to express local immuno-suppressive molecules which inhibit the activity of maternal immune cells.

An immunologically naive cell or other donor cell can be modified to express genes encoding, for example, alternative MHC or immuno-suppressive molecules which confer immune evasive characteristics. Such a broad spectrum donor cell, or similarly, any of the donor cells described previously, can be tested for immunological compatibility by determining its immunogenicity in the presence of recipient immune cells. Methods for determining immunogenicity and criteria for compatibility are well known in the art and include, for example, a mixed lymphocyte reaction, a chromium release assay or a natural killer cell assay. Immunogenicity can be assessed by culturing donor cells together with lymphocyte effector cells obtained from a diabetic individual and measuring the survival of the donor cell targets. The extent of survival of the donor cells is indicative of, and correlates with, the viability of the cells following implantation.

The cells of the invention can originate from essentially any tissue or organ. For primary cells, a tissue should be selected that is easily accessible and contains cells that exhibit desirable growth and expression characteristics such as those described above. Additional considerations when selecting a tissue source include choice of a tissue that contains cells that can be isolated, cultured and modified to express insulin in a glucose-regulated manner. Examples of sources of tissues include muscle, liver, or skin tissue, as well as venous and hematopoietic tissue. Therefore, cell types within these tissues that can be modified to express insulin in a glucose-regulated manner can be isolated. Such cell types include, for example, muscle (smooth, skeletal or cardiac), fibroblast, liver, fat, hematopoietic, epithelial, endothelial, endocrine, exocrine, kidney, bladder, spleen, stem and germ cells. Other cell types are similarly known in the art that are capable of being modified to express insulin in a glucose-regulated manner and can similarly be obtained or isolated from a tissue source as selected above. Although human tissue sources are advantageous for therapeutic purposes, the species of origin of the cells can be devised from essentially any mammal, so long as the cells exhibit the characteristics that allow for expression of insulin in a glucose-regulated manner.

The invention also provides a method for producing an isolated population of insulin-secreting cells by transducing cells with a vector of the invention and isolating the transduced cells. An isolated population of cells can be obtained or isolated by a variety of methods, and the selected method will depend on the type, location, and desired use of the cells. Methods for isolating cell populations are well known in the art as described below. Alternatively, cells which have been previously characterized and isolated can be obtained from a commercial source, such as a tissue or cell bank (American Type Culture Collection, Rockville, Md.) and used directly for modification. The isolated cells should contain a sufficient or effective number of cells of the desired type which can be modified to express insulin in a glucose-regulated manner. Moreover, the population of cells can comprise one or more cell types so long as an effective number can be modified to express insulin in a glucose-regulated manner. Therefore, populations of the glucose-regulated insulin producing cells of the invention can be composed of a single cell type, all of which are modified to express insulin in a glucose-controlled manner, or multiple cell types, where each cell type is modified to express glucose regulated insulin. Alternatively, the populations of glucose-regulated insulin producing cells of the invention can be composed of two or more cell types, where at least one cell type is modified to express insulin in a glucose-regulated manner. Such heterogeneous populations can provide advantages in therapeutic applications where cell viability of implanted cells is augmented by the presence of accessory cells. A specific example of such heterogenous cell populations would be those derived from fetal tissue sources.

Any of the cell types described above can be used to produce the cell or populations of the invention. One example of a cell type that is useful in prosthetic grafts is a fibroblast cell. Fibroblast cells can be obtained from a variety of tissue sources such as, for example, skin, liver, muscle or arterial tissue. Fibroblast cells are also advantageous in that they are easily obtained and isolated, easily modified, and can proliferate to higher densities within a graft. For example, a 10 cm$^2$ piece of prosthetic graft can contain $10^8$ fibroblast cells, or up to 20 layers of cells, and can express glucose-regulated insulin at therapeutic levels.

Cells to be used in a prosthetic graft can require use of an adherent cell type, which would require use of isolation methods that temporarily digest or release the cells from their surrounding tissue. For example, smooth muscle cells can be obtained from a segment of venous or arterial tissue. The smooth muscle cells can be obtained following enzymatic digestion in trypsin and collagenase and purified by positive selection using muscle cell-specific antigens such as von Willebrand factor (Lejnieks et al., *Blood,* 92:1–7 (1998). Alternatively, cells can be isolated following digestion and further purified by centrifugation. The centrifugation can be performed in the presence of a gradient such as a sucrose gradient, which would allow for further separation of cell populations based on their density. Methods for the isolation of primary cells from a tissue source are well known in the art (see, for example, Freshney, *Animal Cell Culture: A Practical Approach,* 2nd ed., IRL Press at Oxford University Press, New York (1992). Maintenance of the cells prior to modification and implantation can be as a cell suspension, adherent cell culture or as organ culture. Conditions for the maintenance and culture of primary and clonal cells are well known in the art.

Once a cell type has been selected as described above, cells expressing proinsulin containing a proinsulin cleavage site and a glucose-regulated protease capable of cleaving the proinsulin cleavage site are generated by introducing a vector expressing the above-described nucleic acid sequences into an appropriate cell. Methods for introducing such vectors into a cell are well known in the art (see for example, Osborne et al., supra (1995)). One method of introducing a vector into a cell is by transfection of plasmid or DNA vectors. Transfection methods are well known in the art and include, for example, calcium phosphate precipitation, electroporation, liposome-mediated transfection, and microinjection as described, for example, in Sambrook et al. supra (1989) and Ausubel et al., supra (1998). Alternatively, a retroviral or adenoviral vector can be transduced into a cell. Methods for transduction of retroviral and adenoviral-type vectors are also well known in the art and are described further in Example I.

Following transfection or transduction of cells with vectors of the invention, the cells are selected using a selectable marker that is either on the same vector as the gene of interest or is co-transfected on a separate vector. Methods of selecting cells for expression of a selectable marker encoded by a transfected vector are well known to those skilled in the art (see, for example, Ausubel et al. supra (1998)). Following selection, an isolated population of cells expressing the gene products of interest is obtained.

Verification that the population of cells expresses proinsulin and protease can be determined using methods well known in the art. For example, a population of cells modified to express proinsulin and protease can be verified for the ability to express insulin in a glucose-regulated manner by assaying the amount of insulin secreted into the culture media in high glucose as compared to low glucose. The level of insulin secreted by the population of cells can then be measured by radioimmunoassay or by a functional assay for one of the known biological functions of insulin such as those listed, for example, in Table 2. An exemplary functional assay could consist of measurement of the rate or quantity of radioactive glucose transfer into a test cell or tissue such as adipose or muscle tissue, or measurement of an increase in fatty acid synthesis in a test cell or tissue when treated with media from the above population of cells being verified. Additional methods of selecting cells containing and expressing proinsulin and insulin include Northern analysis and solution hybridization of mRNA obtained from the cells, in situ hybridization, immunohistology, and immunofluorescence using antibodies specific for proinsulin, protease or insulin. Further selection of a population of cells suitable for use in the invention can be performed using in vivo models. For example, the population of cells of the invention useful for treating diabetes can be verified for their ability to induce glucose homeostasis in diabetic rats treated with the cells as compared to diabetic rats not treated with the cells.

Once a population of cells has been obtained, the cells can be implanted directly into a patient, processed as prosthetic grafts, frozen for long-term storage, or maintained in culture prior to implantation into a diabetic individual, depending on the need. It is understood that even a single cell expressing proinsulin and a protease is useful in the invention. A single cell can be useful, for example, if the level of expression of bioactive insulin produced by the cell is sufficient to ameliorate or alleviate a sign or symptom of diabetes or is sufficient to prevent onset of diabetes or reduce the severity of the disease.

The invention also provides a method of treating or preventing diabetes by implanting into an individual cells coexpressing proinsulin containing a proinsulin cleavage site and a glucose-regulated protease capable of cleaving proinsulin to produce insulin. A diabetic individual requiring glucose-regulated insulin secretion can be treated with the above-described population of cells by a variety of implantation methods. An individual suitable for treatment with the cells of the invention is selected using clinical criteria and prognostic indicators of diabetes that are well known in the art. Definite clinical diagnosis of at least one of the symptoms of diabetes or pathologies related to diabetes as described previously herein would warrant administration of the cells of the invention. A list of exemplary pathological symptoms is included in Table 1.

An individual at risk of developing diabetes as assessed by known prognostic indicators such as family history, fasting blood glucose levels, or decreased glucose tolerance also warrant administration of cells modified to express proinsulin and protease in a glucose-regulated manner. One skilled in the art would recognize or know how to diagnose an individual with diabetes or disregulated glucose uptake and, depending upon the degree or severity of the disease, can make the appropriate determination of when to administer the claimed invention and can also select the most desirable mode of administration. For example, whereas a person with long-standing type 1 disease can require immediate implantation of the insulin expressing cells, a person with long-standing type 2 disease could defer treatment until after there is an indication of a lack of effectiveness of other prescribed treatments.

A population of cells expressing glucose-regulated insulin can be administered to an individual that has been determined by one skilled in the art to require treatment for diabetes for amelioration of their disease. The cells can be administered for amelioration of one or more signs or symptoms of diabetes. For example, a diabetic individual can be implanted with the cells following diagnosis of the disease. The implanted cells will express insulin in response to increased blood glucose levels such as following ingestion of a meal so that glucose homeostasis is at least partially restored. An individual that has been effectively treated for diabetes will exhibit a reduction in severity of at least one of the symptoms indicative of the disease following implantation of the insulin secreting cells. The reduction in severity of a symptom can be determined and would be apparent to one skilled in the art.

Individuals with less severe diabetes can also be implanted with the insulin expressing population of cells of the invention. Determination of a need for treatment in such individuals can be made by one skilled in the art. For example, a diabetic individual that does not respond or responds poorly to standard treatment methods can be treated by methods of the invention. A patient with type 2 disease who has tried unsuccessfully to maintain a long-term decrease in weight or to adhere to an exercise regimen, for example, can be treated for their insulin resistance by implantation of a population of cells of the invention.

The methods of the invention can also be used to improve the efficacy of other therapies for diabetes. The methods of the invention can be used in combination with pre-existing or other methods of treatment to improve the efficacy or ease of use of the other methods. For example, the insulin expressing cells can be implanted in a patient receiving daily injections of insulin or a patient using an insulin pump. Implantation of the cells can reduce the frequency of insulin injections in such a patient. A diabetic individual not receiving insulin therapy but receiving behavioral modification therapy, for example, diet and exercise to decrease weight, can also be implanted with the insulin expressing cells of the invention. Implantation of the insulin expressing cells in such individuals, in combination with a weight reduction and exercise regimen, can decrease the likelihood of disease relapse or can ameliorate signs or symptoms of the disease. The insulin expressing cells of the invention can also be used to treat a diabetic individual having autoimmune responses against endogenous insulin secreting cells. Such diabetic individuals are often treated by immunotherapeutic intervention of the autoimmune response. These individuals can be additionally treated with the population of cells expressing glucose-regulated insulin to achieve greater therapeutic efficacy than would be achieved with immunotherapy alone.

The cell populations of the invention, which express glucose-regulated insulin, can be administered to the individual to produce an increase in insulin secretion and thereby effect a glucose-uptake response. Engraftment of the cells allows prolonged glucose homeostasis due to the expression of insulin. An individual suffering from diabetes can be implanted with a population of insulin expressing cells, for example, smooth muscle cells engineered to express proinsulin and a glucose-regulated protease, seeded onto a prosthetic graft. Such an individual could have a fasting blood glucose level of about 140 mg/dl or greater. Smooth muscle cells can be obtained from the same patient by vein biopsy and then transduced with the above described vectors. Expression of glucose-regulated insulin by the prosthetic graft can ameliorate symptoms of diabetes in the patient for an extended period of time.

A population of cells suitable for implantation consists of a size or cell number that is within a range that can be obtained, modified to express insulin in a glucose-regulated manner, and introduced into an individual. The size of the population of cells is sufficient to express quantities of glucose-regulated insulin that is of therapeutic benefit when implanted in vivo. The size of the above population of cells is preferably about $10^8$ cells, and can be between about $10^6$ to $10^8$ cells, for example, about $10^6$ or about $10^7$ cells, and can be less than about $10^6$ cells. Choice of cell number will depend on the source of the cells, the viability of the cells following implantation, and the level of insulin expression required. One skilled in the art will know, using methods well known in the art, how to determine the appropriate number of cells that produce a therapeutic effect.

Implantation of cells of the invention expressing glucose-regulated insulin can be by a variety of routes. In addition to implantation as a prosthetic graft, a population of cells can also be administered into an individual directly, such as by direct injection intravenously, intramuscularly, subcutaneously, intraperitoneally, or into a tissue or organ site. Cells or compositions to be used for direct administration are obtained and prepared by methods well known in the art and suspended in the appropriate carrier, which can be determined by one skilled in the art. For example, the isolated population of cells can be infused either directly through a catheter connected to a device containing the cells and the catheter inserted into a vein, or can be injected directly into a tissue. The cells are injected in a pharmaceutically acceptable carrier which is defined above and further discussed below. The cells can also be administered with other components such as matrix components, fragments or other molecules which facilitate adhesion of the cells. The cells can be administered in single or multiple administrations as necessary to achieve sufficient expression of therapeutic levels of glucose-regulated insulin.

Alternatively, the cells can be grown on solid matrices or prosthetics, or encapsulated in semi-permeable membranes or barriers prior to insertion into an individual. The individual treated with the cells can then be monitored for efficacy of the treatment by measurement of levels of insulin that is secreted following ingestion of a meal. This could consist of radioimmunoassay measurement of blood levels of insulin following a meal. Alternatively, measurement of fasting blood glucose levels in the individual following implantation of the cells can be used to determine efficacy of the treatment. A decreased rate of glucose disposal as determined by a glucose tolerance test can also be used to verify efficacy of the treatment. Additionally, the alleviation of at least one of the symptoms associated with diabetes can also be used to determine efficacy of the treatment. One skilled in the art would know the appropriate means of evaluating and diagnosing efficacy of the treatment.

The cells are encapsulated or grown on materials that are biocompatible in that they generally will be inert and will not induce or minimally induce an immune response. Such biocompatible materials include, for example, polytetrafluoroethylene (PTFE), surgical grade stainless steel and DACRON.

The invention can also be used for the prevention of diabetes. For example, a population of cells expressing glucose-regulated insulin can be implanted as a prophylactic into individuals at risk of developing diabetes or suffering from hyperglycemia. The invention can also be used, for example, in individuals genetically predisposed to developing diabetes or in obese individuals at risk for developing insulin resistance or disregulated hyperglycemia. These individuals can be implanted with cells expressing glucose-regulated insulin secretion prior to or during the onset of clinically overt hyperglycemia. The latter case can be considered as preventing the disease but can also be considered as treating the disease because normal glucose homeostasis is obtained before chronic elevated blood glucose levels are indicated.

In addition to transfecting cells for implantation into an individual, the vectors of the invention can also be directly administered to an individual for genetic modification, for example, for ex vivo and in vivo therapy. The characteristics of a vector useful for ex vivo and in vivo therapy is generally similar to the characteristics of vectors useful for targeting cells to generate a population of cells expressing glucose-regulated insulin as described above. Viral vectors are particularly advantageous for ex vivo and in vivo therapy.

For example, ex vivo therapy can be carried out essentially as described above except that cells are administered directly to the individual rather than being encapsulated in a matrix. For example, cells can be isolated from an individual as described above and transduced with a viral vector encoding genes sufficient to express glucose-regulated insulin. Methods of ex vivo therapy are well known in the art, for example, as described by Kay et al., *Proc. Natl. Acad. Sci. USA* 89:89–93 (1992); Chowdhury et al., *Science* 254:1802–1805 (1991); and Grossman et al., *Nature Genetics* 6:335–341 (1994).

The use of a viral vector is particularly advantageous for ex vivo and in vivo therapy because viruses typically infect and propagate in specific cell types. Moreover, the natural specificity of viruses for specific tissues or cell types can be used to target a nucleic acid molecule encoding proinsulin in vivo to a particular tissue or limited number of tissues. Furthermore, both viral and non-viral vectors can be modified with specific receptors or ligands to alter target specificity through receptor mediated events.

Retroviral vectors are particularly useful in methods of the invention directed to ex vivo and in vivo therapy. As described in Example I, retroviral vectors were used to express therapeutic levels of insulin in implanted cells. Retroviral vectors can similarly be used in ex vivo and in vivo therapy. Adenovirus and adeno-associated virus can also be used as vectors for ex vivo and in vivo therapy and are particularly advantageous if infection of non-dividing cells is desired. Methods of constructing vectors for ex vivo and in vivo therapeutic use are well known in the art as described, for example, by Kay et al., *Hepatoloay* 21:815–819 (1995); Stratford-Perricaudet et al., *J. Clin. Invest.,* 90:626–630 (1992); and Barr et al., *Gene Therapy,* 2:151–155 (1995).

The vectors of the invention containing an expressible nucleic acid encoding proinsulin containing a proinsulin cleavage site and a glucose-regulated protease can be introduced directly into an individual. The vector to be administered to an individual can be formulated as a pharmaceutical composition comprising the proinsulin and protease expressing nucleic acid sequences and a pharmaceutically acceptable carrier. Pharmaceutically acceptable carriers are well known in the art and include aqueous solutions such as water, physiologically buffered saline, or other solvents or vehicles such as glycols, glycerol, oils such as olive oil or injectable organic esters.

A pharmaceutically acceptable carrier can contain physiologically acceptable compounds that act for example, to stabilize or increase the absorption of the expressible nucleic acid sequences. One skilled in the art would know that the choice of a pharmaceutically acceptable carrier, including a physiologically acceptable compound, depends, for example, on the route of administration of the proinsulin and protease expressing vector and on the particular characteristic of the expression vector, for example, whether the vector is a viral or plasmid vector.

The pharmaceutical composition also can be incorporated, if desired, into oil-in-water emulsions, microemulsions, micelles, mixed micelles, liposomes, microspheres or other polymer matrices (Gregoriadis, *Liposome Technology,* Vols. I to III, 2nd ed., CRC Press, Boca Raton, Fla. (1993); Fraley et al., *Trends Biochem Sci.,* 6:77 (1981). Liposomes, for example, which consist of phospholipids or other lipids, are nontoxic, physiologically acceptable and metabolizable carriers that are relatively simple to make and administer. In addition, liposomes are particularly useful because they can encapsulate the expressible nucleic acid sequences with high efficiency while not compromising the biological activity of the agent, preferentially and substantially bind to a target cell, and deliver the aqueous contents of the vesicle into the target cell with high efficiency (see Mannino et al., *Biotechniques* 6:682 (1988)).

Targeting of a liposome for delivery of a vector of the invention to an individual can be passive or active. Passive targeting, for example, uses the tendency of liposomes to accumulate in cells of the reticuloendothelial system (RES) and in an organ such as the liver, which contains sinusoidal capillaries. The expression vectors formulated as liposomes can be infused directly into the portal vein of the liver and will effectively modify liver cells to express insulin due to the concentration of RES cells in the liver and the sinusoidal nature of the circulatory system in the liver. Active targeting of liposomes containing an expression vector can be achieved by coupling a specific ligand to the liposome. Such ligands include a monoclonal antibody, a sugar, a glycolipid or a protein such as a ligand for a receptor expressed by the target cells. Either method of targeting can be selected depending on the type of cell or location of tissue to be modified for insulin expression.

A vector of the invention encoding proinsulin and a protease is administered in an amount and regimen that will be effective to the individual. Generally, the dosage will be about that typical for administration of nucleic acids and can be determined by one skilled in the art. An effective amount will depend on the degree of severity of the disease in the individual and the level of glucose-regulated insulin expression desired. If the vector is a virus, the vector particles can be administered in an amount from 1 plaque forming unit to about $10^{14}$ plaque forming units, but can also be from about $10^6$ plaque forming units to about $10^{13}$ plaque forming units. The viral vector is purified to a concentration ranging from about 0.25% to 25%, preferably about 5% to 20% before formulation. After formulation, a dose of about 1 pg to 100 ng viral vector is contained in approximately 0.1 ml to 1.0 ml of the pharmaceutical composition.

Administration of a vector containing an expressible nucleic acid sequence to an individual can be as a single treatment or as multiple treatments depending on the level of insulin expression desired or on the number of cells to be modified. Methods for the delivery of nucleic acid sequences encoding for a polypeptide are known in the art as described, for example, by Felgner et al., U.S. Pat. No. 5,580,859, issued Dec. 3, 1996.

The level of modification of cells by a vector containing an expressible nucleic acid sequence encoding proinsulin and a protease useful in the invention is sufficient to result in secretion of a therapeutic level of glucose-regulated insulin. Multiple administrations can also be performed to increase the proportion of modified cells, to increase the number of copies of proinsulin and protease per cell, or to maintain the effective number of modified cells for a desired duration. Efficacy of the in vivo treatment is achieved if at least one of the symptoms of diabetes is alleviated or reduced. A reduction in severity of a symptom of diabetes in a treated individual can be determined as described previously by one skilled in the art.

The following examples are intended to illustrate but not limit the present invention.

EXAMPLE I

Expression of Therapeutic Levels of Insulin

This example demonstrates that a population of non-islet cells can be modified to express glucose-regulated insulin at levels sufficient to treat diabetes.

Studies were performed to demonstrate that non-β islet cells can be modified to express insulin at therapeutic levels. Vascular smooth muscle cells were transduced with a retroviral vector constructed to express human proinsulin I (SEQ ID NO:1) and shown to be capable of expressing mature insulin at high levels. Using standard molecular biology techniques, a retroviral vector LhISN, in which human proinsulin cDNA is expressed from the viral LTR promoter/enhancer and the selectable marker neo gene is driven by the SV40 promoter was constructed and obtained at a titer of $3 \times 10^6$ cfu/ml. This vector was based on constructs previously described for expression of human adenosine deaminase (ADA) (Hock et al., supra (1989), purine nucleoside phosphorylase (PNP) (Osborne et al., supra (1988), dog granulocyte-colony stimulating factor (G-CSF) (Osborne et al., Clinical Research, 41:194A (1994) and rat erythropoietin (Epo) (Osborne et al., supra (1995). The resulting amount of proinsulin and insulin secreted by the transduced cells was then determined using radioimmunoassay for insulin with anti-insulin antibodies which cross react with proinsulin.

PA 317 mouse packaging cells and primary rat vascular smooth muscle cells (SMC) transduced with the above vector secreted high levels of proinsulin. PA 317 packaging cells secreted 26 munits of proinsulin/day/$10^6$ cells and primary rat SMC secreted 92 munits of proinsulin/day/$10^6$ cells.

In order to effectively treat diabetes using methods of the invention, a level of insulin sufficient to regulate glucose levels is secreted by a population of cells that can be feasibly implanted in vivo. Diabetic BB rats receive 20–40 units of long-acting insulin per day in a single injection. Thus, the therapeutic levels of insulin required is within the range of insulin secreted by $10^6$ to $10^7$ transduced cells. This cell number is in the range that can be harvested and implanted in vivo (Lejnieks et al., supra (1996); Osborne et al. supra (1995)). Therefore, an isolated population of non-islet cells can express mature insulin at levels sufficient to treat diabetes when implanted into a diabetic individual.

Expression of insulin in a glucose-regulated manner was demonstrated by use of a single, three gene retroviral vector construct designed to express proinsulin and the protease, furin, which cleaves the proinsulin into bioactive insulin.

A three gene retroviral vector, LrIFNTαFu (FIG. 1) is constructed to express rat or human proinsulin I cDNA (purchased from ATCC, Rockville Md.), neomycin phosphotransferase (neo) and murine furin (Creemers et al., supra (1992)). Expression of the furin cDNA is designed to be under the control of promoter elements from rat TGF-α (McClain et al., supra (1992)). The rat proinsulin coding DNA is placed in the vector pLXFN. The selectable neo gene (N) is then placed 3' to a foot-and-mouth disease internal ribosome entry site to give pLIFN (Ramesh et al., supra (1996)). The rat TGFα promoter is placed 5' to the furin sequence and the resulting 2.65 kb fragment is placed 3' to the neo gene to obtain the pLrIFNTαFu vector.

Amphotropic retroviral vectors are produced from PE 501/PA 317 packaging cells (Miller et al., Mol. Cell. Biol. 6:2895–2902 (1986)) and titered using NIH 3T3 cells (Osborne et al., supra (1988); Osborne et al., Hum. Gene. Ther. 1:31–41 (1990)). Proviral integrity in packaging and primary smooth muscle cells is then determined by Southern analysis and vector plasmids are sequenced with an Applied Biosystems PE 310 automated capillary electrophoresis DNA sequencer. Replication competent viruses are then screened by a sensitive $S^+L^-$ assay (Miller et al., supra (1986); Miller et al., Somat. Cell. Mol. Genet. 12:175–183 (1986)). Verification that these retroviral vector constructs express therapeutic levels of insulin in response to changes in glucose levels is then shown using primary diabetic BB rat and rat vascular smooth muscle cells (SMC).

Primary diabetic BB rat cells and SMC are infected and selected in G418 and conditioned media and assayed for levels of mature insulin secreted in response to increased glucose. An increase in secreted insulin in response to increasing glucose concentration in the culture from normal (5.5 mM glucose) to high (30 mM glucose) shows that the transduced cells secrete insulin in a glucose-regulated manner. The levels of insulin secreted by an implantable number of cells ($10^6$–$10^7$) is determined by RIA as described above and will be within the range sufficient for in vivo treatment of diabetes.

Further enhancement of glucose-regulated insulin expression was demonstrated using a vector encoding for proinsulin containing a specific protease cleavage site. In this approach, a furin cleavable site was introduced into the human proinsulin cDNA to produce a mutant human proinsulin (I*). The retroviral vector, pLI*FNTαFu, which is depicted in FIG. 1, contains the mutated human proinsulin (I*) in place of the wild-type human proinsulin encoding sequence.

Non-islet cells are capable of synthesizing bioactive insulin when transfected with a proinsulin cDNA that has been mutated to contain furin cleavable sites. Co-transfection of furin along with the mutated proinsulin cDNA further augments the levels of mature insulin that is expressed by the non-islet cells (Yanagita et al., FEBS Letters 311:55–59 (1992)). Use of this proinsulin/furin expression system allows for a rapid and enhanced glucose-regulated insulin response to elevated levels of glucose and which is described and shown below.

To obtain mutated proinsulin, furin cleavable tetrabasic processing sites were initially introduced into human pre-proinsulin cDNA (Bell et al., supra (1979); Sures et al., supra (1980); Chekhranova et al., supra (1992)). The sequence encoding this site consists of: Arg-Xaa-Lys/Arg-Arg (SEQ ID NO:8) and allows for maximum (100%) furin-mediated enzymatic conversion of proinsulin to bioactive insulin. The resulting mutant preproinsulin cDNA was then placed under control of LTR in the pLXSN vector to generate pLhI*SN, and a TGFαFu fragment was inserted 5' to SV40-neo to give LhI*TαFuSN, where furin was under the control of the TGFα promoter. PA317 virus packaging cells were transduced and showed a 4.3-fold increased insulin secretion when cultured in high glucose (629 units/ml insulin) as compared to secretion when cultured in low glucose (148 units/ml insulin). These results demonstrate that an implantable population of cells can be engineered to express therapeutic levels of glucose-regulated insulin and that the rate of insulin secretion can be further enhanced by use of a proinsulin/furin expression system due to the inherent ability of furin to catalyze cleavage of multiple substrate molecules.

Additional augmentation of glucose-regulated insulin expression was demonstrated in studies using an additional vector encoding for a glutamine:fructose-6-phosphate amidotransferase (GFA). Increased expression of bioactive insulin by an implantable population of cells can be further achieved by transduction of a second vector containing GFA. Transfection of cDNA for GFA, the rate limiting enzyme in the hexosamine synthetic pathway that involves glucosamine, leads to a 50 to 100 fold glucose-sensitive up-regulation in TGFα promoter activity in rat SMC (Sayeski et al., supra (1994); McKnight et al., *J. Biol. Chem.* 267:25208–25212 (1992)). This enhancement is achieved because the TGFα promoter is 10-fold more sensitive to glucosamine than to glucose (Raja et al., supra (1991)). Thus, cells can be engineered to be exquisitely responsive to glucose by stable integration of GFA, in addition to the proinsulin-furin-neo construct.

The second transduction step is accomplished using a vector employing histidine dehydrogenase (HisD) as a selectable marker and histidinol as a selective agent (Stockschlader et al., *Hum Gene. Ther.* 2:33–39 (1991)). The vector LGFASHisD is constructed from LSHisD by insertion of a murine GFA cDNA (Sayeski et al., supra (1994)).

Primary vascular smooth muscle cells are robust and able to tolerate this double infection/selection procedure. An isolated population of cells at a number which can be feasibly implanted into a diabetic host ($10^6$–$10^7$ cells) is transduced with the three-gene retroviral vector expressing proinsulin, neo and furin under the control of TGFα promoter elements and a vector expressing GFA. The cells are then tested for their ability to convert proinsulin to mature insulin in response to changes in glucose level by RIA of mature insulin secreted into the media at low levels of glucose and at high levels of glucose. Results from the RIA are used to verify that an implantable population of cells express glucose-regulated insulin secretion at levels that are sufficient for therapeutic efficacy in vivo.

The results described above demonstrate that non-islet cells can express high levels of mature insulin in response to hyperglycemia, that this expression is rapid and under tight-glucose regulation, and that the insulin level is expressed from a population of cells whose size is in the range that can be implanted in vivo are levels of insulin having therapeutic benefit.

EXAMPLE II

Treatment of Diabetic Rats by Insulin Expression from Prosthetic Grafts Implanted in the Stomach This example demonstrates that smooth muscle cells transduced with the glucose-regulated insulin expressing vectors are therapeutically effective when implanted into diabetic rats.

Vascular smooth muscle cells transduced with the above-described vectors are implanted in diabetic BB rats using a prosthetic graft placed into the stomach wall. Prosthetic grafts are constructed by seeding transduced cells in the procedure as described below.

Rat smooth muscle cells are isolated from aorta using enzymatic digestion and characterized by positive staining for muscle cell specific actins with the HHF35 antibody, while staining negative for von Willebrand factor (an endothelial cell specific marker). For transplantation, Fisher 344 rats are anesthetized and a 3-cm midline abdominal incision from the xyphoid to the umbilicus is made. The stomach is temporarily exteriorized and a superficial 0.5 cm incision is made in the capsule on the cranial face of the stomach body. A small pocket (0.6 cm diameter) is created under the capsule of the stomach using blunt dissection and a small PTFE ring is then inserted into the pocket and sutured in place using 5-0 maxon thread. The PTFE rings are placed under the serosal plane of the stomach. The suture material is drawn tightly to constrict the ring to a final diameter of 2–3 mm before finishing the knot. The fibrous tunic directly overlying the ring is cryofrozen using a steel probe, and the ring is mechanically elevated.

The inserted graft as described above consists of a ring (4 mm inner diameter, 6 mm outer diameter) of polytetrafluoroethylene (PTFE) to retain and provide a niche for the transduced cells (Osborne et al., supra (1993); Osborne et al., supra (1995); Dale et al., *Blood* 81:2496–2502 (1993)). Smooth muscle cells transduced with the glucose-regulated insulin and GFA expression vectors are injected at $10^6$ cells/50 μl media into the center of the ring through a 24-g intravenous (IV) catheter. Animals receive two rings each containing the transduced cells. The diabetic rats are then monitored for insulin and glucose levels. Rats containing the stomach implants will show a long-term regulated decrease in blood glucose levels to euglycemia, resulting from insulin secretion in response to hyperglycemia. The use of prosthetic grafts for long-term sustained expression of vector-encoded genes at levels which achieve therapeutic efficacy can be achieved in vivo and are described below.

In a study analogous to the rat model of diabetes described above, long-term in vivo efficacy of prosthetic grafts expressing an erythropoietin (Epo) gene was verified in rats using the procedures described above. Animals which had been treated with implants containing cells transduced with the erythropoietin gene showed elevated hematocrits and demonstrated that retrovirally transduced smooth muscle cells allowed sustained expression of the transduced genes over the long-term (Osborne et al, supra (1995).

Nine rats received prosthetic grafts containing cells transduced with a erythropoietin expressing vector. The prosthetic grafts were implanted as described above. Following implantation, the prosthetic graft became vascularized and permitted the proliferation and long-term survival of the transduced smooth muscle cells. Implantation into the stomach wall protected the transduced cells from ingrowth of non-transduced cells. The prosthetic graft became vascularized, thus permitting the proliferation and long-term survival of transduced smooth muscle cells. Histological examination of a PTFE ring from one of the rats at 1 year showed that the tissue within and around the PTFE graft was fully integrated, well vascularized and that the transduced smooth muscle cells were contained within the PTFE ring (Lejnieks et al., supra(1998)).

Figure 2:
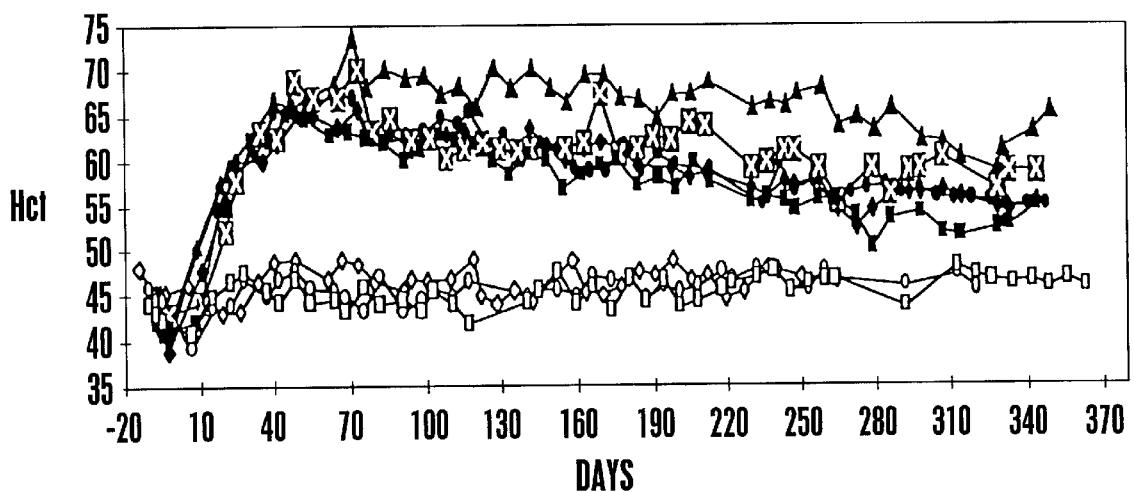
FIG. 2 shows the hematocrit analysis of rats implanted with prosthetic stomach grafts consisting of smooth muscle cells transduced with either rat erythropoietin (Epo) or human adenosine deaminase (ADA).

Hematocrits of animals containing Epo-expressing prosthetic grafts rose over 2 months from a mean of 42.6±1.4% pre-surgery to range between 55% to 70% over the 12 month test period (FIG. 2). All treated animals maintained a mean hematocrit of 60%±4.7%. Hemoglobin levels in these animals rose from a pre-surgery mean of 15.2±0.4 g/dl to a seven week maximum of 22.6±2.0 g/dl with a mean of 20.6±1.4 g/dl. The hematocrits and hemoglobin levels of control animals (animals treated with human ADA encoding vector) remained unchanged. Thus, prosthetic grafts seeded with transduced vascular smooth muscle cells implanted by a PTFE stomach patch sustained gene expression for greater than a year. These results demonstrate and verify that smooth muscle cells can be implanted in vivo as prosthetic grafts and that the engrafted transduced cells maintain long-term expression of vectors transduced into the smooth muscle cells at levels sufficient for therapeutic efficacy.

Efficacy of using prosthetic grafts containing transduced cells for sustained vector encoded gene expression was also demonstrated in additional animal models. Baboons were implanted with prosthetic PTFE grafts containing autologous vascular SMC (Geary et al., *Hum. Gene Ther.* 5:1213–1218, 1994). Retroviral vectors encoding β-galactosidase (LNPoZ) or a control gene, human purine nucleoside phosphorylase (LPNSN-2), were transduced into autologous baboon SMC. The SMC were obtained from vein biopsies. Transduced cells were placed into a collagen solution and seeded onto the luminal surface of the grafts. One LNPoZ-seeded graft and one LPNSN-2-seeded control graft was implanted bilaterally into the aorto-iliac circulation of each of 4 animals. All grafts remained patent until they were removed after 3–5 weeks and examined histologically for vector-expressing cells.

Histological examination of the prosthetic grafts containing β-galactosidase-vector seeded cells showed positive blue staining with the X-gal chromogen in all of the animal. No sections from the control grafts contained stainable cells. Smooth muscle cells expressing the reporter gene were localized within the graft wall but not in the newly forming intima or outer capsule of fibrous tissue. These results further demonstrate that a population of cells implanted in vivo via prosthetic grafts provides sustained vector encoded gene expression. Use of this type of graft will be effective in providing therapeutic long-term systemic glucose-regulated insulin secretion in diabetic patients.

Figure 3A:
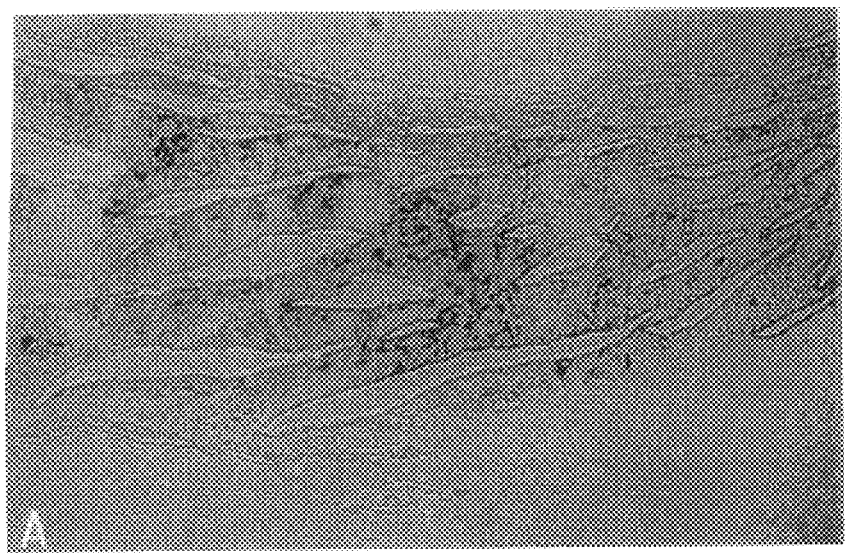
FIG. 3 shows β-galactosidase (β-gal) expression and hematoxylin and eosin staining of cross sections of prosthetic vascular grafts consisting of smooth muscle cells transduced with β-gal expressing virus. The prosthetic grafts were implanted in the femoral artery of dogs.
Figure 3B:
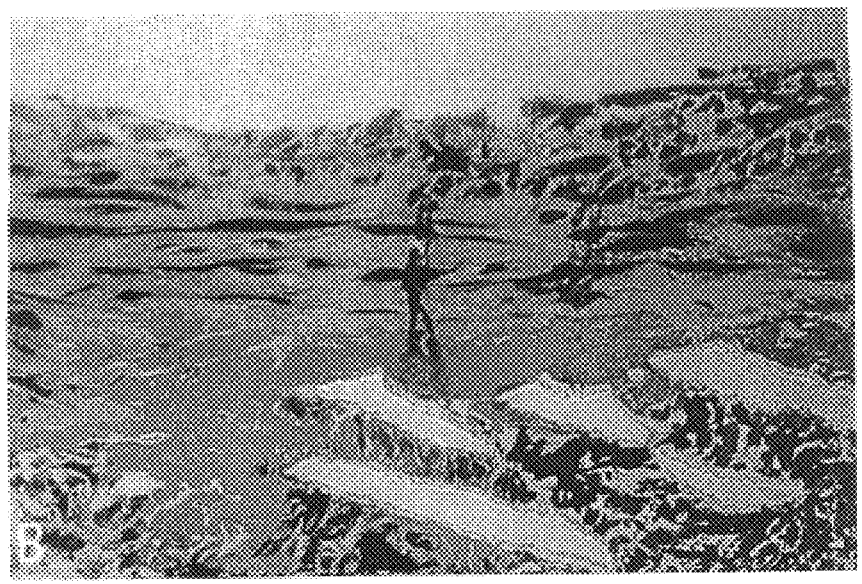

In an additional related animal model, a different method of obtaining prosthetic grafts was used to implant smooth muscle cells containing G-CSF or β-gal encoding vector into dogs. Cells were seeded into the prosthetic graft without using collagen polymerization. The grafts containing seeded cells were cultured for 5–7 days prior to surgical implantation. This resulted in the formation of a mature cell matrix within the graft which allowed for an increased number of cells for implantation. Autologous endothelial cells were also seeded onto the graft luminal surface 24 hrs prior to surgery to reduce thrombosis. The grafts were implanted as two 6 cm shunts in the left and right femoral arteries of dogs. At intervals, 1 cm sections of graft were removed and stained for β-gal activity. A section of graft removed at 7 days showed a wide, uniform distribution of transduced cells (FIG. 3). A graft section obtained at 11 days showed layers of transduced cells constituting a new intimal surface, with adjacent transduced cells in the graft wall (FIG. 3). This alternative method of cell seeding allowed for a large increase in the number of transduced cells within the graft matrix, an even distribution of cells throughout the graft wall, and formation of a new intimal surface by the transduced cells.

Using the same alternative method of cell seeding described above, expression of G-CSF by prosthetic grafts in a dog model of canine cyclic hematopoiesis also resulted in long-term levels of vector encoded gene expression and at therapeutic levels. The interstices of a PTFE graft were seeded with SMC transduced to express canine G-CSF with autologous non-transduced endothelial cells seeded onto the luminal surface. Neutrophil counts were monitored before and after implantation of two 5 cm grafts implanted as described above. In one dog, neutrophils increased 43% from a mean count of 5,450 neutrophils/$\mu$l before surgery to 7,790 neutrophils/$\mu$l after surgery, giving a net increase of 2,340 neutrophils/$\mu$l over the 88 day observation period. In a second animal observed for 35 days, neutrophils increased by 50% after surgery as compared to neutrophil levels before surgery. Responses of this magnitude may be more than adequate to improve the clinical status of patients with cyclic or chronic neutropenia. These results further demonstrate the efficacy of using prosthetic grafts implanted with cells genetically modified to supply sustained glucose-regulated insulin for treatment of diabetes.

Throughout this application, various publications have been referenced. The disclosures of these publications in their entireties are hereby incorporated by reference in this application in order to more fully describe the state of the art to which this invention pertains.

Although the invention has been described with reference to the examples provided above, it should be understood that various modifications can be made without departing from the spirit of the intention. Accordingly, the invention is limited only by the claims.

What is claimed is:

1. An isolated population of cells comprising an expressible nucleic acid encoding proinsulin containing a proinsulin cleavage site and a glucose-regulated expressible nucleic acid encoding an exogenous protease capable of cleaving said proinsulin cleavage site to produce insulin.

2. The isolated population of claim 1, wherein said protease is furin.

3. The isolated population of claim 1, wherein said glucose-regulated expressible nucleic acid further comprises a transforming growth factor-α (TGF-α) regulatory element.

4. The isolated population of claim 1, wherein said proinsulin and said protease are expressed from a single vector.

5. The isolated population of claim 4, wherein said vector is a retroviral vector.

6. The isolated population of claim 4, wherein said vector further comprises a selectable marker.

7. The isolated population of claim 1, wherein said cells are smooth muscle cells.

8. The isolated population of claim 1, wherein said proinsulin cleavage site further comprises the following tetrabasic sequence comprising the amino acids:

Arg-Xaa-Lys/Arg/Xaa-Arg (SEQ ID NO:7), wherein Xaa comprises any amino acid.

9. A three-gene vector comprising an expressible nucleic acid encoding proinsulin containing a proinsulin cleavage site, a glucose-regulated expressible nucleic acid encoding a protease capable of cleaving said proinsulin cleavage site to produce insulin, and a selectable marker.

10. The three-gene vector of claim 9, wherein said protease is furin.

11. The three-gene vector of claim 9, wherein said glucose-regulated expressible nucleic acid further comprises a TGF-α regulatory element.

12. The three-gene vector of claim 9, wherein said selectable marker is neomycin phosphotransferase.

13. The three-gene vector of claim 9, wherein said proinsulin cleavage site further comprises a tetrabasic sequence comprising the amino acids:

Arg-Xaa-Lys/Arg/Xaa-Arg (SEQ ID NO:7).

14. The three-gene vector of claim 9 wherein said vector is a retroviral vector.

15. A method for producing an isolated population of insulin-secreting cells, comprising transducing cells with the three-gene vector of claim 11 and isolating said transduced cells.

* * * * *

UNITED STATES PATENT AND TRADEMARK OFFICE
CERTIFICATE OF CORRECTION

PATENT NO. : 6,537,806 B1
DATED : March 25, 2003
INVENTOR(S) : Osborne et al.

It is certified that error appears in the above-identified patent and that said Letters Patent is hereby corrected as shown below:

Title page,
Item [56], References Cited, U.S. PATENT DOCUMENTS, please add -- 6,348,327, and 6,352,857 --.

Column 44,
Line 9, please delete "claim 11" replace therefor with -- claim 9 --.

Signed and Sealed this

Twenty-fifth Day of May, 2004

JON W. DUDAS
*Acting Director of the United States Patent and Trademark Office*

SEQUENCE LISTING

```
<160> NUMBER OF SEQ ID NOS: 11

<210> SEQ ID NO 1
<211> LENGTH: 450
<212> TYPE: DNA
<213> ORGANISM: Homo sapiens
<220> FEATURE:
<221> NAME/KEY: CDS
<222> LOCATION: (45)..(377)

<400> SEQUENCE: 1
gctgcatcag aagaggccat caagcacatc actgtccttc tgcc atg gcc ctg tgg     56
```

```
                        Met Ala Leu Trp
                         1 atg cgc ctc ctg ccc ctg ctg gcg ctg ctg gcc ctc tgg gga cct gac       104
Met Arg Leu Leu Pro Leu Leu Ala Leu Leu Ala Leu Trp Gly Pro Asp
 5              10                  15                  20 cca gcc gca gcc ttt gtg aac caa cac ctg tgc ggc tca cac ctg gtg       152
Pro Ala Ala Ala Phe Val Asn Gln His Leu Cys Gly Ser His Leu Val
             25                  30                  35 gaa gct ctc tac cta gtg tgc ggg gaa cga ggc ttc ttc tac aca ccc       200
Glu Ala Leu Tyr Leu Val Cys Gly Glu Arg Gly Phe Phe Tyr Thr Pro
             40                  45                  50 aag acc cgc cgg gag gca gag gac ctg cag gtg ggg cag gtg gag ctg       248
Lys Thr Arg Arg Glu Ala Glu Asp Leu Gln Val Gly Gln Val Glu Leu
         55                  60                  65 ggc ggg ggc cct ggt gca ggc agc ctg cag ccc ttg gcc ctg gag ggg       296
Gly Gly Gly Pro Gly Ala Gly Ser Leu Gln Pro Leu Ala Leu Glu Gly
 70                  75                  80 tcc ctg cag aag cgt ggc att gtg gaa caa tgc tgt acc agc atc tgc       344
Ser Leu Gln Lys Arg Gly Ile Val Glu Gln Cys Cys Thr Ser Ile Cys
 85                  90                  95                 100 tcc ctc tac cag ctg gag aac tac tgc aac tag acgcagcccg caggcagccc    397
Ser Leu Tyr Gln Leu Glu Asn Tyr Cys Asn
                 105                 110 cccacccgcc gcctcctgca ccgagagaga tggaataaag cccttgaacc agc            450

<210> SEQ ID NO 2
<211> LENGTH: 110
<212> TYPE: PRT
<213> ORGANISM: Homo sapiens

<400> SEQUENCE: 2

Met Ala Leu Trp Met Arg Leu Leu Pro Leu Leu Ala Leu Leu Ala Leu
 1               5                  10                  15

Trp Gly Pro Asp Pro Ala Ala Ala Phe Val Asn Gln His Leu Cys Gly
                 20                  25                  30

Ser His Leu Val Glu Ala Leu Tyr Leu Val Cys Gly Glu Arg Gly Phe
             35                  40                  45

Phe Tyr Thr Pro Lys Thr Arg Arg Glu Ala Glu Asp Leu Gln Val Gly
         50                  55                  60

Gln Val Glu Leu Gly Gly Gly Pro Gly Ala Gly Ser Leu Gln Pro Leu
 65                  70                  75                  80

Ala Leu Glu Gly Ser Leu Gln Lys Arg Gly Ile Val Glu Gln Cys Cys
                 85                  90                  95

Thr Ser Ile Cys Ser Leu Tyr Gln Leu Glu Asn Tyr Cys Asn
             100                 105                 110

<210> SEQ ID NO 3
<211> LENGTH: 63
<212> TYPE: DNA
<213> ORGANISM: Homo sapiens
<220> FEATURE:
<221> NAME/KEY: CDS
<222> LOCATION: (1)..(63)

<400> SEQUENCE: 3 ggc att gtg gaa caa tgc tgt acc agc atc tgc tcc ctc tac cag ctg       48
Gly Ile Val Glu Gln Cys Cys Thr Ser Ile Cys Ser Leu Tyr Gln Leu
 1               5                  10                  15 gag aac tac tgc aac                                                    63
Glu Asn Tyr Cys Asn
```

```
<210> SEQ ID NO 4
<211> LENGTH: 21
<212> TYPE: PRT
<213> ORGANISM: Homo sapiens

<400> SEQUENCE: 4

Gly Ile Val Glu Gln Cys Cys Thr Ser Ile Cys Ser Leu Tyr Gln Leu
  1               5                  10                  15

Glu Asn Tyr Cys Asn
            20

<210> SEQ ID NO 5
<211> LENGTH: 90
<212> TYPE: DNA
<213> ORGANISM: Homo sapiens
<220> FEATURE:
<221> NAME/KEY: CDS
<222> LOCATION: (1)..(90)

<400> SEQUENCE: 5 ttt gtg aac caa cac ctg tgc ggc tca cac ctg gtg gaa gct ctc tac      48
Phe Val Asn Gln His Leu Cys Gly Ser His Leu Val Glu Ala Leu Tyr
  1               5                  10                  15 cta gtg tgc ggg gaa cga ggc ttc ttc tac aca ccc aag acc              90
Leu Val Cys Gly Glu Arg Gly Phe Phe Tyr Thr Pro Lys Thr
                20                  25                  30

<210> SEQ ID NO 6
<211> LENGTH: 30
<212> TYPE: PRT
<213> ORGANISM: Homo sapiens

<400> SEQUENCE: 6

Phe Val Asn Gln His Leu Cys Gly Ser His Leu Val Glu Ala Leu Tyr
  1               5                  10                  15

Leu Val Cys Gly Glu Arg Gly Phe Phe Tyr Thr Pro Lys Thr
                20                  25                  30

<210> SEQ ID NO 7
<211> LENGTH: 4
<212> TYPE: PRT
<213> ORGANISM: Artificial Sequence
<220> FEATURE:
<221> NAME/KEY: SITE
<222> LOCATION: (2)
<223> OTHER INFORMATION: any amino acid
<220> FEATURE:
<221> NAME/KEY: SITE
<222> LOCATION: (3)
<223> OTHER INFORMATION: lysine or arginine or any amino acid
      (Lys/Arg/Xaa)
<220> FEATURE:
<223> OTHER INFORMATION: Description of Artificial Sequence: Consensus
      Sequence

<400> SEQUENCE: 7

Arg Xaa Xaa Arg
  1

<210> SEQ ID NO 8
<211> LENGTH: 4
<212> TYPE: PRT
<213> ORGANISM: Artificial Sequence
<220> FEATURE:
<221> NAME/KEY: SITE
```

```
<222> LOCATION: (2)
<223> OTHER INFORMATION: any amino acid
<220> FEATURE:
<221> NAME/KEY: SITE
<222> LOCATION: (3)
<223> OTHER INFORMATION: Lysine or Arginine (Lys/Arg)
<220> FEATURE:
<223> OTHER INFORMATION: Description of Artificial Sequence: Consensus
      Sequence

<400> SEQUENCE: 8

Arg Xaa Xaa Arg
 1

<210> SEQ ID NO 9
<211> LENGTH: 5
<212> TYPE: PRT
<213> ORGANISM: Artificial Sequence
<220> FEATURE:
<223> OTHER INFORMATION: Description of Artificial Sequence: Consensus
      Sequence

<400> SEQUENCE: 9

Asp Asp Asp Asp Lys
 1               5

<210> SEQ ID NO 10
<211> LENGTH: 4
<212> TYPE: PRT
<213> ORGANISM: Artificial Sequence
<220> FEATURE:
<223> OTHER INFORMATION: Description of Artificial Sequence: Consensus
      Sequence

<400> SEQUENCE: 10

Ile Glu Gly Arg
 1

<210> SEQ ID NO 11
<211> LENGTH: 4
<212> TYPE: PRT
<213> ORGANISM: Artificial Sequence
<220> FEATURE:
<221> NAME/KEY: SITE
<222> LOCATION: (2)
<223> OTHER INFORMATION: any amino acid
<220> FEATURE:
<223> OTHER INFORMATION: Description of Artificial Sequence: Consensus
      Sequence

<400> SEQUENCE: 11

Arg Xaa Lys Arg
 1
```